(12) United States Patent
Snow et al.

(10) Patent No.: US 11,490,918 B2
(45) Date of Patent: *Nov. 8, 2022

(54) APPARATUS FOR ENDOSCOPIC PROCEDURES

(71) Applicant: Covidien LP, Mansfield, MA (US)

(72) Inventors: Josh Snow, Clinton, CT (US); Philip Irka, Madison, CT (US); Ethan Collins, Naugatuck, CT (US); Joseph Costanzo, Hatfield, PA (US); Anthony Calderoni, Bristol, CT (US); Michael Ingmanson, Stratford, CT (US); Timothy Wells, Ridgefield, CT (US); Thomas Wingardner, III, North Haven, CT (US); Ramiro Cabrera, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 532 days.

This patent is subject to a terminal disclaimer.

(21) Appl. No.: 16/700,115

(22) Filed: Dec. 2, 2019

(65) Prior Publication Data

US 2020/0100805 A1 Apr. 2, 2020

Related U.S. Application Data

(63) Continuation of application No. 13/932,313, filed on Jul. 1, 2013, now Pat. No. 10,492,814.
(Continued)

(51) Int. Cl.
*A61B 17/32* (2006.01)
*A61B 17/068* (2006.01)
(Continued)

(52) U.S. Cl.
CPC .... *A61B 17/320016* (2013.01); *A61B 17/068* (2013.01); *A61B 17/07207* (2013.01);
(Continued)

(58) Field of Classification Search
CPC .......... A61B 17/320016; A61B 17/068; A61B 17/07207; A61B 2017/00115;
(Continued)

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

AU 2008229795 A1 4/2009
CA 2451558 A1 1/2003
(Continued)

OTHER PUBLICATIONS

International Search Report corresponding to PCT/US2005/027266, completed May 30, 2008 and dated Jun. 18, 2008; (2 pp.).
(Continued)

*Primary Examiner* — George J Ulsh
*Assistant Examiner* — Rachel S Highland
(74) *Attorney, Agent, or Firm* — Carter, DeLuca & Farrell LLP

(57) ABSTRACT

A surgical device is provided. The surgical device includes a jaw assembly defining a first longitudinal axis and including a first jaw and a second jaw moveable relative to the first jaw; an elongated body defining a second longitudinal axis and coupled to a proximal end of the jaw assembly, wherein the jaw assembly is configured to articulate about an articulation axis transverse to the second longitudinal axis relative to the elongated body; and a handle assembly coupled to a proximal end of the elongated body and including at least one motor mechanically coupled to the jaw assembly and a control assembly including a first control button and a second control button, wherein actuation of the first control button moves the second jaw in approximation relative to
(Continued)

the first jaw and actuating the second control button moves the second jaw away from the first jaw, and actuating the first and second control buttons moves the jaw assembly to a centered position in which the first and second longitudinal axes are substantially aligned, the handle assembly further includes an illumination member configured to output a light pattern indicative of a status of the surgical instrument.

13 Claims, 20 Drawing Sheets

Related U.S. Application Data

(60) Provisional application No. 61/669,253, filed on Jul. 9, 2012.

(51) Int. Cl.
*A61B 17/072* (2006.01)
*A61B 17/00* (2006.01)
*A61B 17/29* (2006.01)
*A61B 90/00* (2016.01)

(52) U.S. Cl.
CPC .......... *A61B 2017/0046* (2013.01); *A61B 2017/00115* (2013.01); *A61B 2017/00128* (2013.01); *A61B 2017/00345* (2013.01); *A61B 2017/00384* (2013.01); *A61B 2017/00389* (2013.01); *A61B 2017/00398* (2013.01); *A61B 2017/00464* (2013.01); *A61B 2017/00473* (2013.01); *A61B 2017/00477* (2013.01); *A61B 2017/00734* (2013.01); *A61B 2017/2903* (2013.01); *A61B 2017/2923* (2013.01); *A61B 2017/2927* (2013.01); *A61B 2017/2929* (2013.01); *A61B 2090/0803* (2016.02); *A61B 2090/0808* (2016.02); *A61B 2090/0811* (2016.02); *A61B 2090/0813* (2016.02); *A61B 2090/0814* (2016.02)

(58) Field of Classification Search
CPC .......... A61B 2017/00128; A61B 2017/00345; A61B 2017/00384; A61B 2017/00389; A61B 2017/00398; A61B 2017/0046; A61B 2017/00464; A61B 2017/00473; A61B 2017/00477; A61B 2017/00734; A61B 2017/2903; A61B 2017/2923; A61B 2017/2927; A61B 2017/2929; A61B 2090/0803; A61B 2090/0808; A61B 2090/0811; A61B 2090/0813; A61B 2090/0814; A61B 90/30; A61B 2090/309
See application file for complete search history.

(56) References Cited

U.S. PATENT DOCUMENTS

| | | | |
|---|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,871,493 A | 2/1999 | Sjostrom et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,494,892 B1 | 12/2002 | Ireland et al. |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |

(56) References Cited

U.S. PATENT DOCUMENTS

| | | |
|---|---|---|
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 3,016,178 A1 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |

(56) References Cited

U.S. PATENT DOCUMENTS

| | | |
|---|---|---|
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2002/0049454 A1 | 4/2002 | Whitman et al. |
| 2002/0072766 A1 | 6/2002 | Hunt et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0044383 A1 | 3/2004 | Woods |
| 2004/0111012 A1 | 6/2004 | Whitman |
| 2004/0133189 A1 | 7/2004 | Sakurai |
| 2004/0176751 A1 | 9/2004 | Weitzner et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0234715 A1 | 9/2008 | Pesce et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0082387 A1 | 4/2011 | Miller et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116364 A1 | 5/2012 | Houser et al. |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |

(56) References Cited

U.S. PATENT DOCUMENTS

| | | | |
|---|---|---|---|
| 2016/0113648 A1 | 4/2016 | Zergiebel et al. | |
| 2016/0113649 A1 | 4/2016 | Zergiebel et al. | |

FOREIGN PATENT DOCUMENTS

| | | | |
|---|---|---|---|
| CN | 101283924 | A | 10/2008 |
| CN | 101856251 | A | 10/2010 |
| CN | 102113902 | A | 7/2011 |
| CN | 102247182 | A | 11/2011 |
| DE | 102008053842 | A1 | 5/2010 |
| EP | 0634144 | A1 | 1/1995 |
| EP | 0648476 | A1 | 4/1995 |
| EP | 0686374 | A2 | 12/1995 |
| EP | 0705571 | A1 | 4/1996 |
| EP | 1690502 | A1 | 8/2006 |
| EP | 1723913 | A1 | 11/2006 |
| EP | 1736112 | A1 | 12/2006 |
| EP | 1759652 | A2 | 3/2007 |
| EP | 1769754 | A1 | 4/2007 |
| EP | 1772105 | A1 | 4/2007 |
| EP | 1774914 | A1 | 4/2007 |
| EP | 1813199 | A1 | 8/2007 |
| EP | 1813203 | A2 | 8/2007 |
| EP | 1813211 | A2 | 8/2007 |
| EP | 1908412 | A2 | 4/2008 |
| EP | 1917929 | A1 | 5/2008 |
| EP | 1943954 | A2 | 7/2008 |
| EP | 1943956 | A2 | 7/2008 |
| EP | 1943958 | A1 | 7/2008 |
| EP | 1943976 | A2 | 7/2008 |
| EP | 1952769 | A2 | 8/2008 |
| EP | 2005898 | A2 | 12/2008 |
| EP | 2027819 | A1 | 2/2009 |
| EP | 2044890 | A1 | 4/2009 |
| EP | 2055243 | A2 | 5/2009 |
| EP | 2090247 | A1 | 8/2009 |
| EP | 2090251 | A2 | 8/2009 |
| EP | 2098170 | A2 | 9/2009 |
| EP | 2100561 | A2 | 9/2009 |
| EP | 2100562 | A2 | 9/2009 |
| EP | 2165664 | A2 | 3/2010 |
| EP | 2236098 | A2 | 10/2010 |
| EP | 2245994 | A1 | 11/2010 |
| EP | 2263568 | A2 | 12/2010 |
| EP | 2272443 | A1 | 1/2011 |
| EP | 2316345 | A1 | 5/2011 |
| EP | 2324776 | A2 | 5/2011 |
| EP | 2329773 | A1 | 6/2011 |
| EP | 2333509 | A1 | 6/2011 |
| EP | 2377472 | A1 | 10/2011 |
| EP | 2462878 | A1 | 6/2012 |
| EP | 2462880 | A2 | 6/2012 |
| EP | 2491872 | A1 | 8/2012 |
| EP | 2586382 | A2 | 5/2013 |
| EP | 2606834 | A2 | 6/2013 |
| EP | 2668910 | A2 | 12/2013 |
| EP | 2676615 | A2 | 12/2013 |
| EP | 2815705 | A1 | 12/2014 |
| ES | 2333509 | A1 | 2/2010 |
| FR | 2861574 | A1 | 5/2005 |
| JP | 08038488 | | 2/1996 |
| JP | 2005125075 | A | 5/2005 |
| JP | 2007508868 | A | 4/2007 |
| JP | 2009233333 | A | 10/2009 |
| JP | 2011115594 | A | 6/2011 |
| KR | 20120022521 | A | 3/2012 |
| WO | 9112773 | A1 | 9/1991 |
| WO | 9915086 | A1 | 4/1999 |
| WO | 0072760 | A1 | 12/2000 |
| WO | 0072765 | A1 | 12/2000 |
| WO | 03000138 | A2 | 1/2003 |
| WO | 03026511 | A1 | 4/2003 |
| WO | 03030743 | A2 | 4/2003 |
| WO | 03065916 | A1 | 8/2003 |
| WO | 03077769 | A1 | 9/2003 |
| WO | 03090630 | A2 | 11/2003 |
| WO | 2004107989 | A1 | 12/2004 |
| WO | 2006042210 | A2 | 4/2006 |
| WO | 2007016290 | A2 | 2/2007 |
| WO | 2007/026354 | A1 | 3/2007 |
| WO | 2007137304 | A2 | 11/2007 |
| WO | 2008131362 | A2 | 10/2008 |
| WO | 2008133956 | A2 | 11/2008 |
| WO | 2009039506 | A1 | 3/2009 |
| WO | 2007014355 | A3 | 4/2009 |
| WO | 2009132359 | A2 | 10/2009 |
| WO | 2009143092 | A1 | 11/2009 |
| WO | 2009149234 | A1 | 12/2009 |
| WO | 2011108840 | A2 | 9/2011 |
| WO | 2012/040984 | A1 | 4/2012 |

OTHER PUBLICATIONS

Extended European Search Report corresponding to EP 08 25 2703.7, completed Oct. 23, 2008 and dated Oct. 31, 2008; (7 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805. 3, dated Nov. 4, 2013.

(56) References Cited

OTHER PUBLICATIONS

Extended European Search Report from Application No. EP 13171742.3 dated Jan. 3, 2014.
Extended European Search Report, dated May 27, 2015, corresponding to European Patent Application No. 15152791.8; 5 pages.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action (with English translation), dated Jul. 1, 2016, corresponding to Chinese Application No. 201310286676.7; 20 total pages.
Chinese Office Action (with English translation), dated May 27, 2017, corresponding to Chinese Application No. 201310286676.7; 21 total pages.
Japanese Office Action (with English translation), dated Apr. 17, 2017, corresponding to Japanese Application No. 2013-142552; 6 total pages.
Extended European Search Report corresponding to European Application No. EP 17 15 3830.9, dated Jul. 20, 2017; 10 pages.
Japanese Notice of Allowance with English Summary Form, corresponding to Japanese Application No. 2013-142552, dated Aug. 1, 2017; 4 total pages.
Australian Examination Report dated Apr. 20, 2018 issued in corresponding Australian Appln. No. 2017203410.
Extended European Search Report corresponding to International Application No. EP 15 17 38071 dated Nov. 24, 2015.
Australian Examination Report for application No. 2013206723 dated Nov. 24, 2016.
Chinese Office Action for Application No. 201310369318.2 dated Jun. 28, 2016.
Chinese Office Action dated Feb. 24, 2017 in corresponding Chinese Patent Application No. 201310369318.2, together with English translation, 14 pages.
Australian Examination Report dated Nov. 30, 2018 issued in corresponding AU Appln. No. 2017203410.
Canadian Office Action dated Mar. 26, 2019 issued in corresponding CA Appln. No. 2,820,156.
Australian Examination Report dated Jul. 31, 2020 issued in corresponding AU Appln. No. 2019204962.

APPARATUS FOR ENDOSCOPIC PROCEDURES

CROSS-REFERENCE TO RELATED APPLICATION

The present application is a continuation of U.S. patent application Ser. No. 13/932,313, filed on Jul. 1, 2013, which claims the benefit of and priority to U.S. Provisional Application No. 61/669,253, filed on Jul. 9, 2012. The entire disclosures of all of the foregoing applications are incorporated by reference herein.

BACKGROUND

1. Technical Field

The present disclosure relates to surgical apparatuses, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. In many instances the electromechanical surgical devices include a reusable handle assembly, and disposable or single use loading units. The loading units are selectively connected to the handle assembly prior to use and then disconnected from the handle assembly following use in order to be disposed of or in some instances sterilized for re-use.

Many of these electromechanical surgical devices include complex drive components that utilize a variety of user interfaces that accept user inputs (e.g., controls) for controlling the devices as well as provide feedback to the user. A need exists for electromechanical surgical apparatus, devices and/or systems having improved user interfaces.

SUMMARY

Further details and aspects of exemplary embodiments of the present invention are described in more detail below with reference to the appended Figures.

According to an embodiment of the present disclosure, a surgical device is provided. The surgical device includes a jaw assembly defining a first longitudinal axis and including a first jaw and a second jaw moveable relative to the first jaw; an elongated body defining a second longitudinal axis and coupled to a proximal end of the jaw assembly, wherein the jaw assembly is configured to articulate about an articulation axis transverse to the second longitudinal axis relative to the elongated body; and a handle assembly coupled to a proximal end of the elongated body and including at least one motor mechanically coupled to the jaw assembly and a control assembly including a first control button and a second control button, wherein actuation of the first control button moves the second jaw in approximation relative to the first jaw and actuating the second control button moves the second jaw away from the first jaw, and actuating the first and second control buttons moves the jaw assembly to a centered position in which the first and second longitudinal axes are substantially aligned.

The control assembly further includes a first rocker switch, wherein actuation thereof is configured to articulate the jaw assembly about the articulation axis.

The jaw assembly is further configured to pivot about the second longitudinal axis relative to the elongated body.

The control assembly further includes a second rocker switch, wherein actuation thereof is configured to rotate the jaw assembly about the second longitudinal axis relative to the elongated body.

The handle assembly further includes an illumination member configured to output a light pattern indicative of a status of the surgical instrument.

The light pattern includes progressive activation of a plurality of lights and the status is a firing progress of the jaw assembly.

The illumination member has a substantially circular shape and includes a plurality of light emitting devices disposed about a circumference of the illumination member.

The illumination member includes an upper portion and a lower portion disposed about a horizontal plane, the upper portion includes a first plurality of light emitting devices and the lower portion includes a second plurality of light emitting devices.

The first plurality of light emitting devices is visible to a first user having a first line of sight above the horizontal plane, and the second plurality of light emitting devices is visible to a second user having a second line of sight below the horizontal plane.

The illumination member further includes at least one side light emitting device disposed on the horizontal plane and on each side of the illumination member, the at least one side light emitting device being visible to the first and second users.

According to an embodiment of the present disclosure, a surgical device is provided. The surgical device includes a jaw assembly defining a first longitudinal axis and including a first jaw and a second jaw moveable relative to the first jaw; an elongated body defining a second longitudinal axis and removably coupled to a proximal end of the jaw assembly, wherein the jaw assembly is configured to articulate about an articulation axis transverse to the second longitudinal axis relative to the elongated body; and a handle assembly removably coupled to a proximal end of the elongated body and including at least one motor mechanically coupled to the jaw assembly and an illumination member configured to output a light pattern indicative of a status of the surgical instrument.

The illumination member has a substantially circular shape and includes a plurality of light emitting devices disposed about a circumference of the illumination member.

The illumination member includes an upper portion and a lower portion disposed about a horizontal plane, the upper portion includes a first plurality of light emitting devices and the lower portion includes a second plurality of light emitting devices.

The first plurality of light emitting devices is visible to a first user having a first line of sight above the horizontal plane, and the second plurality of light emitting devices is visible to a second user having a second line of sight below the horizontal plane.

The illumination member further includes at least one side light emitting device disposed on the horizontal plane and on each side of the illumination member, the at least one side light emitting device being visible to the first and second users.

The first plurality of light emitting devices is configured to output a light pattern indicative of a firing progress of the jaw assembly.

The second plurality of light emitting devices is configured to output a light pattern indicative of a status of each of the jaw assembly, the elongated body, and the handle assembly.

The first plurality of light emitting devices is configured to output a light pattern indicative of a number of remaining of uses of at least one of the elongated body or the handle assembly.

The illumination member further includes at least one side light emitting device disposed on the horizontal plane and on each side of the illumination member, the at least one side light emitting device being visible to the first and second users.

The light emitting device is configured to output a light pattern indicative of an error state with at least one of the jaw assembly, the elongated body, or the handle assembly.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
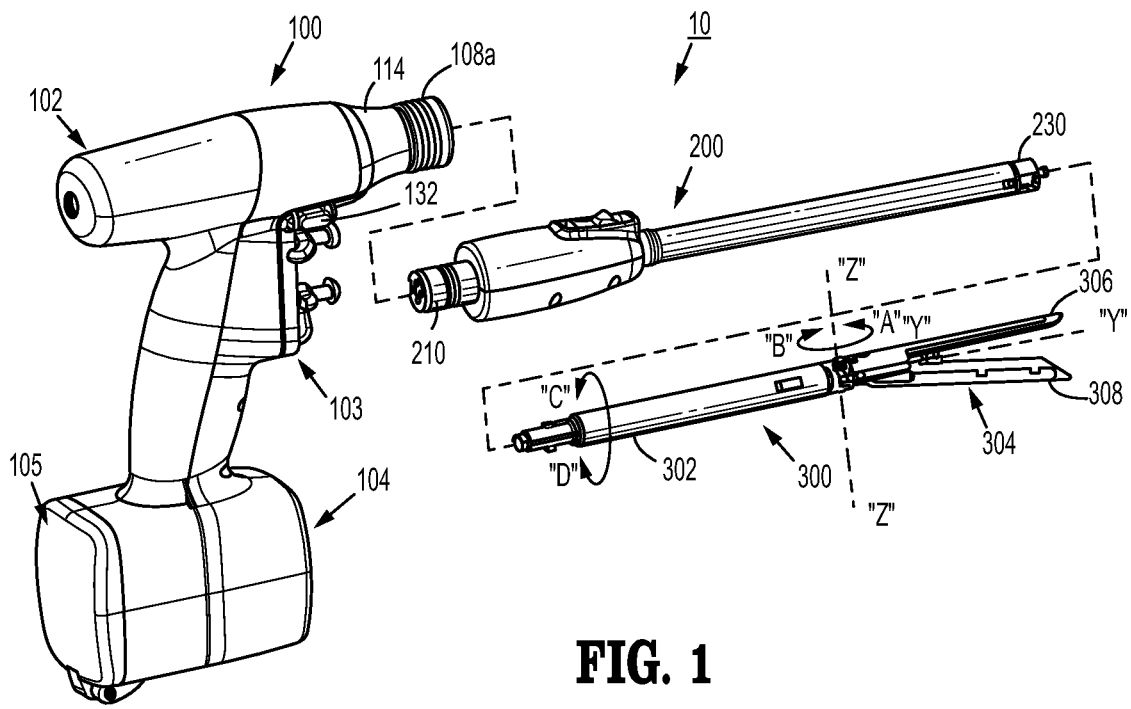
FIG. 1 is a perspective, disassembled view of an electromechanical surgical system including a surgical instrument, an elongated member, and an end effector, according to the present disclosure.

Embodiments of the presently disclosed electromechanical surgical system, apparatus and/or device are described in detail with reference to the drawings, in which like reference numerals designate identical or corresponding elements in each of the several views. As used herein the term "distal"

refers to that portion of the electromechanical surgical system, apparatus and/or device, or component thereof, that are farther from the user, while the term "proximal" refers to that portion of the electromechanical surgical system, apparatus and/or device, or component thereof, that are closer to the user. The terms "left" and "right" refer to that portion of the electromechanical surgical system, apparatus and/or device, or component thereof, that are on the left (e.g., port) and right (e.g., starboard) sides, respectively, from the perspective of the user facing the distal end of the electromechanical surgical system, apparatus and/or device from the proximal end while the surgical system, apparatus and/or device is oriented in non-rotational configuration.

Referring initially to FIGS. 1-8, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 300, via an adapter assembly 200 (e.g., elongated body). The end effector 300 and the adapter assembly 200 are configured for actuation and manipulation by the electromechanical, hand-held, powered surgical instrument 100. In particular, the surgical instrument 100, the adapter assembly 200, and the end effector 300 are separable from each other such that the surgical instrument 100 is configured for selective connection with adapter assembly 200, and, in turn, adapter assembly 200 is configured for selective connection with any one of a plurality of different end effectors 300.

Reference may be made to International Application No. PCT/US2008/077249, filed Sep. 22, 2008 (Inter. Pub. No. WO 2009/039506) and U.S. Patent Application Publication No. 2011/0121049, filed on Nov. 20, 2009, the entire contents of all of which are incorporated herein by reference, for a detailed description of the construction and operation of exemplary electromechanical, hand-held, powered surgical instrument 100.

Figure 2:
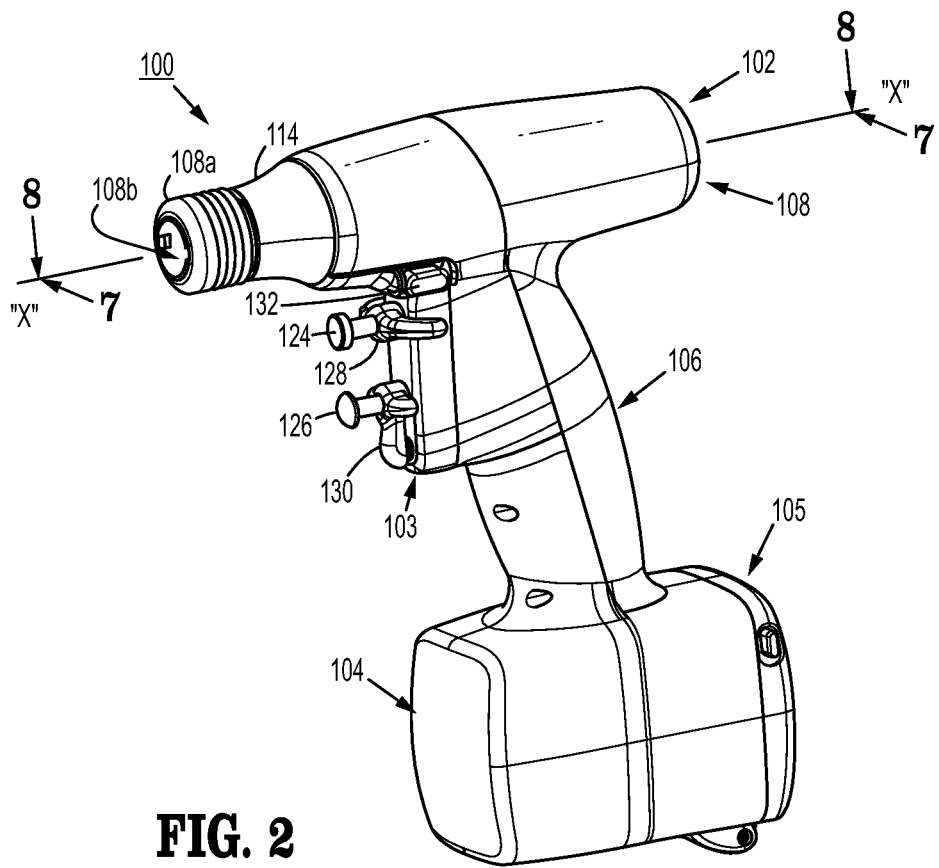
FIG. 2 is a perspective view of the surgical instrument of FIG. 1, according to the present disclosure.
Figure 3:
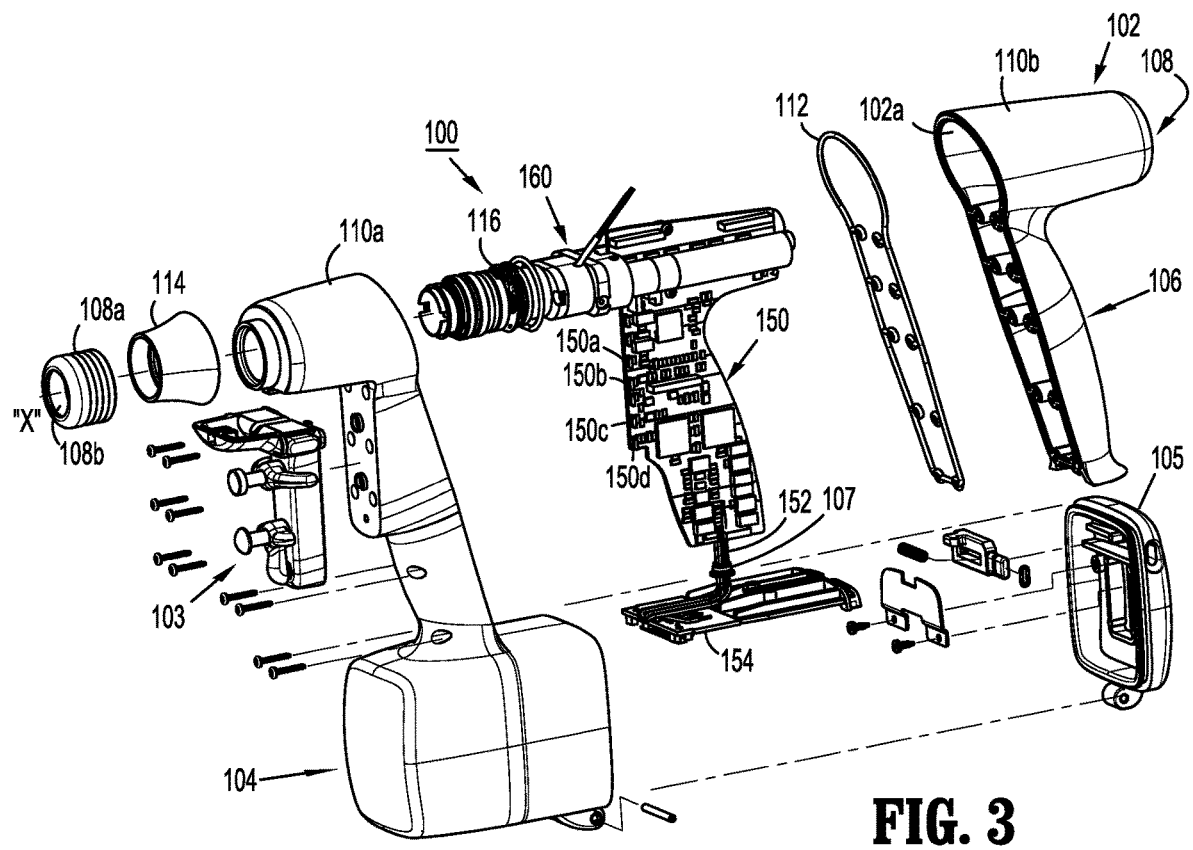
FIG. 3 is perspective, exploded view of the surgical instrument of FIG. 1, according to the present disclosure.

As illustrated in FIGS. 1-3, surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

With reference to FIGS. 2 and 3, distal and proximal half-sections 110a, 110b are divided along a vertical plane that traverses a longitudinal axis "X-X" of upper housing portion 108. Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical instrument 100, as will be set forth in additional detail below.

Figure 4:
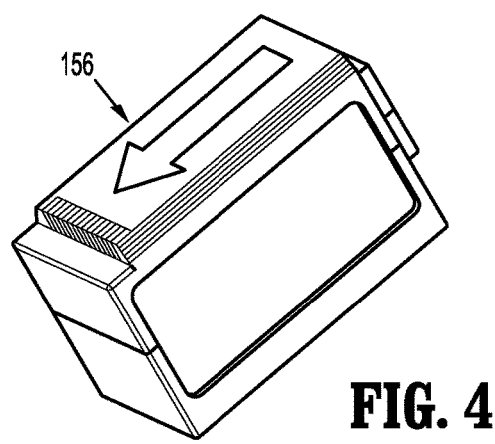
FIG. 4 is a perspective view of a battery of the surgical instrument of FIG. 1, according to the present disclosure.

Lower housing portion 104 of surgical instrument 100 defines an aperture (not shown) formed in an upper surface thereof and which is located beneath or within intermediate housing portion 106. As shown in FIGS. 3 and 4, the aperture of lower housing portion 104 provides a passage through which wires 152 pass to electrically interconnect electrical components situated in lower housing portion 104, e.g., a battery 156 and a circuit board 154, with electrical components situated in intermediate housing portion 106 and/or upper housing portion 108, e.g., circuit board 150, drive mechanism 160, etc.

Handle housing 102 includes a gasket 107 disposed within the aperture of lower housing portion 104 (not shown) thereby plugging or sealing the aperture of lower housing portion 104 while allowing wires 152 to pass therethrough. Gasket 107 functions to establish an air-tight seal between lower housing portion 106 and intermediate housing portion 108 such that circuit board 150 and drive mechanism 160 are protected from sterilization and/or cleaning procedures.

With continued reference to FIGS. 3 and 4, lower housing portion 104 of handle housing 102 provides a housing in which the battery 156 is removably disposed therein. The battery 156 may be a rechargeable battery (e.g., lead-based, nickel-based, lithium-ion based, etc.). It is also envisioned that the battery 156 may be a single-use, non-rechargeable battery. Battery 156 is configured to supply power to any of the electrical components of surgical instrument 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

Figure 5:
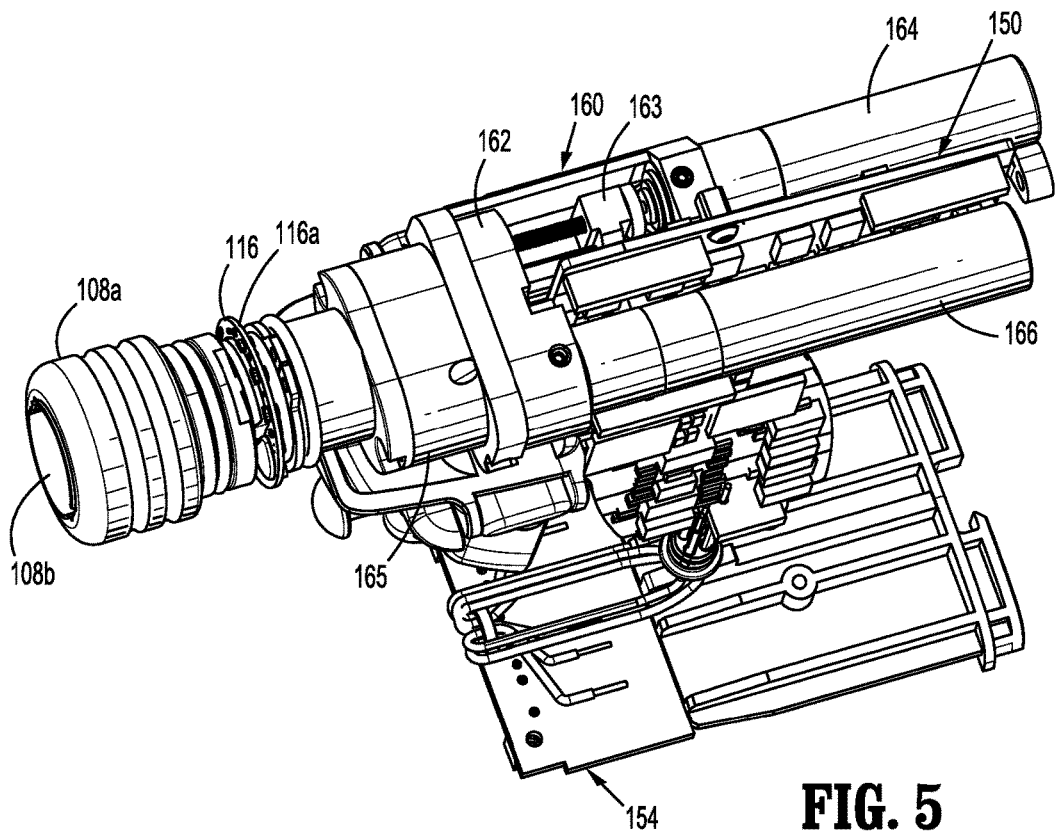
FIG. 5 is a top, partially-disassembled view of the surgical instrument of FIG. 1, according to the present disclosure.

With continued reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent, light-transmissive material. An illumination member 116 is disposed within nose cone 114 such that illumination member 116 is visible therethrough. The nose cone 114 may be tinted, such that the illumination member 116 is visible when it is activated.

With reference to FIG. 5, the illumination member 116 may include a plurality of any suitable light emitting devices, such as light emitting diodes (LEDs), disposed on printed circuit board (LED PCB) 116a which is disposed in a vertical plane transverse to the longitudinal axis "X-X." The illumination member 116 is configured to illuminate in multiple colors with a specific color pattern being associated with a unique discrete event. In embodiments, the LEDs may be single-color or multi-color LEDs.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical instrument 100. In particular, drive mechanism 160 is configured to drive shafts and/or gear components in order to selectively move tool assembly 304 of end effector 300 relative to proximal body portion 302 of end effector 300, to rotate end effector 300 about the longitudinal axis "X-X" (FIG. 3) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter assembly 200. Proximal to the selector gearbox assembly 162 is a function selection module 163 having a first (e.g., selector) motor 164 that functions to selectively move gear elements within the selector gearbox assembly 162 into engagement with an input drive component 165 having a second (e.g., drive) motor 166.

As illustrated in FIGS. 1-4, distal half-section 110a of upper housing portion 108 defines a connecting portion 108a configured to accept a corresponding drive coupling assembly 210 of adapter assembly 200.

Figure 6:
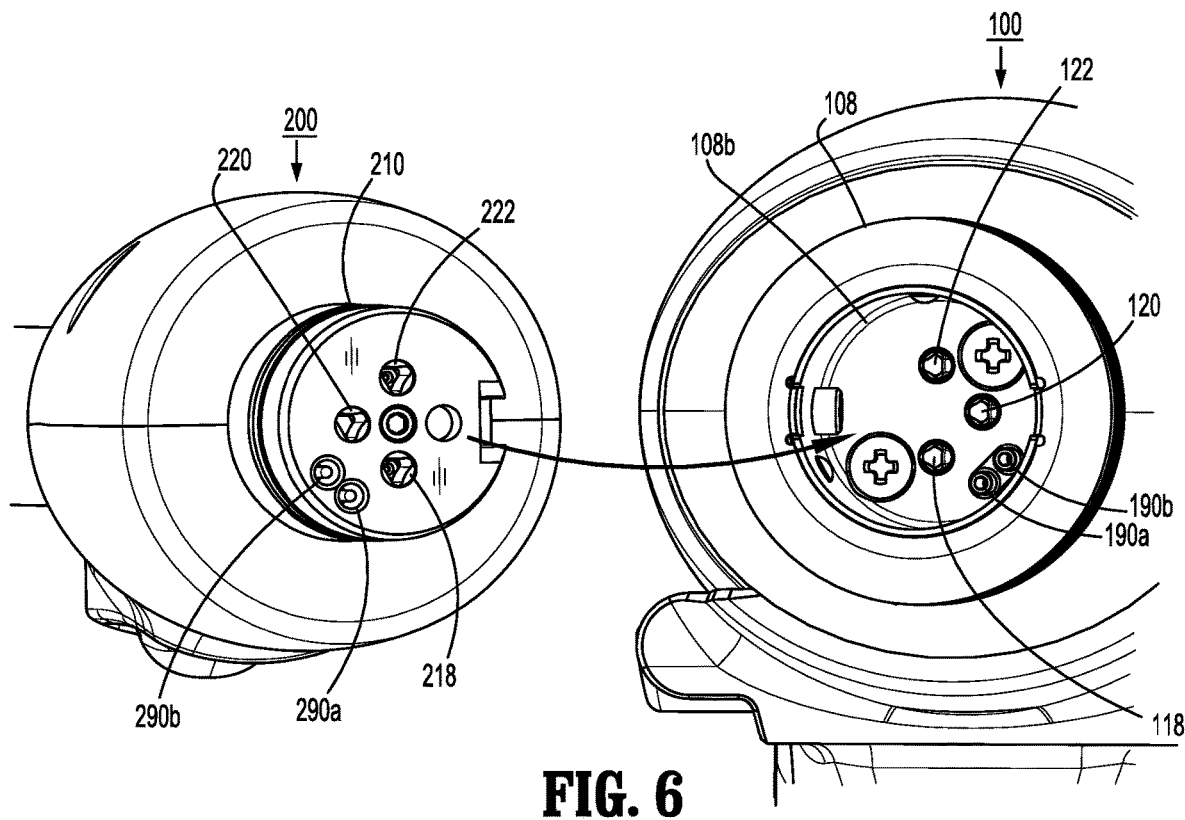
FIG. 6 is a front, perspective view of the surgical instrument of FIG. 1 with the elongated member separated therefrom, according to the present disclosure.
Figure 7:
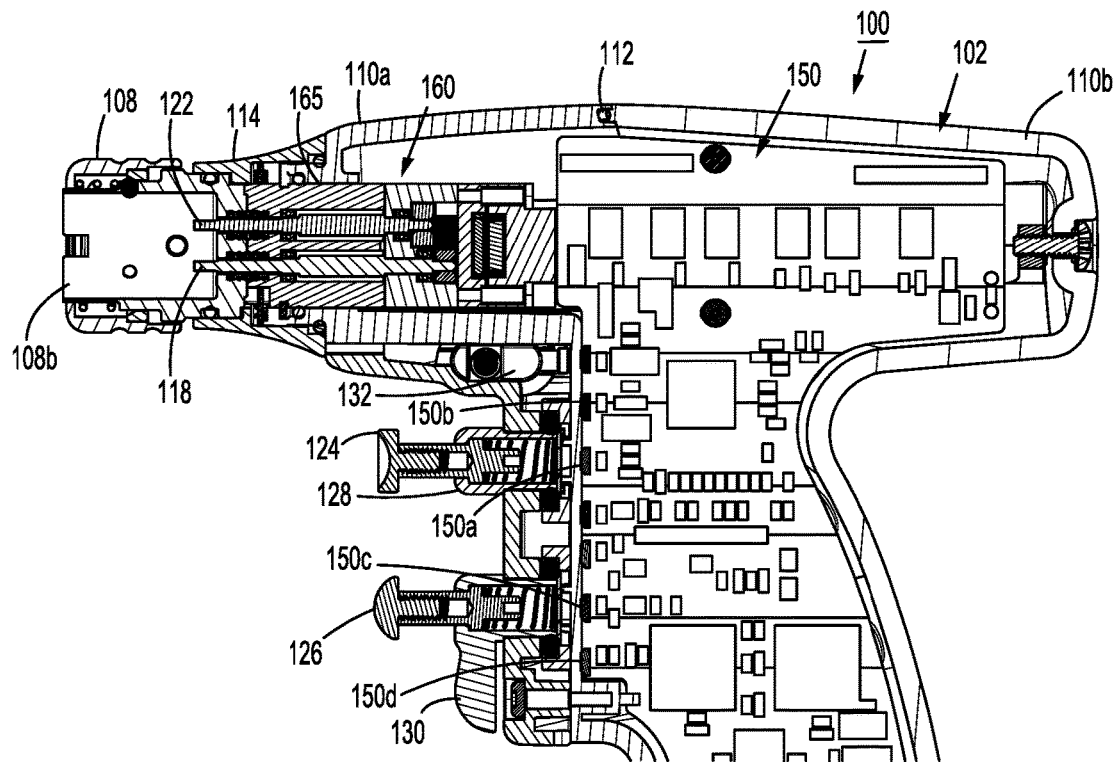
FIG. 7 is a side, cross-sectional view of the surgical instrument of FIG. 1, as taken through 7-7 of FIG. 1, according to the present disclosure.
Figure 8:
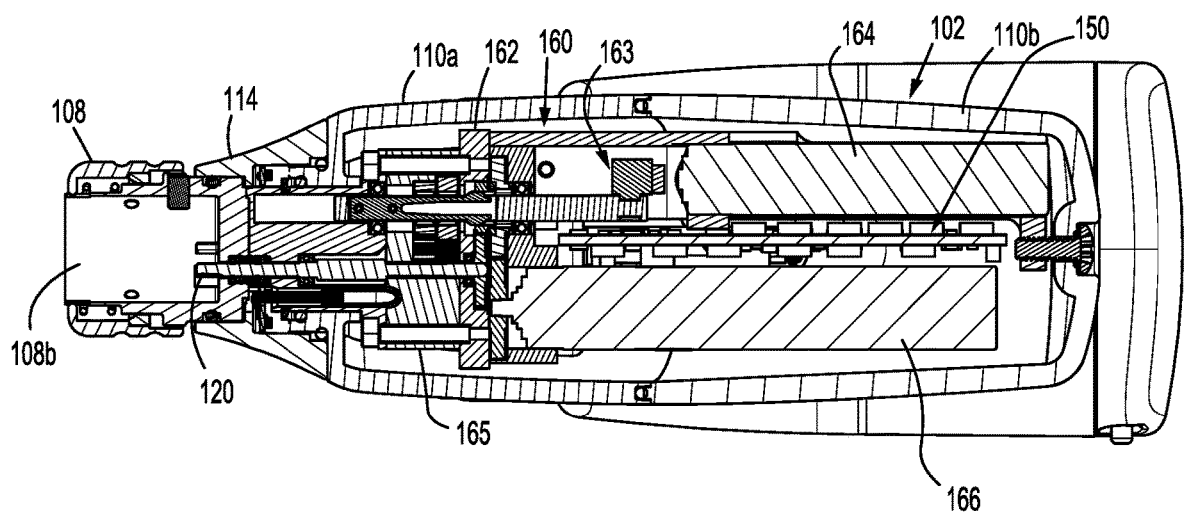
FIG. 8 is a top, cross-sectional view of the surgical instrument of FIG. 1, as taken through 8-8 of FIG. 1, according to the present disclosure.

As illustrated in FIGS. 6-8, connecting portion 108a of surgical instrument 100 has a cylindrical recess 108b that receives a drive coupling assembly 210 of adapter assembly 200 when adapter assembly 200 is mated to surgical instrument 100. Connecting portion 108a houses three rotatable drive connectors 118, 120, 122.

With reference to FIG. 6, when adapter assembly 200 is mated to surgical instrument 100, each of rotatable drive connectors 118, 120, 122 of surgical instrument 100 couples with a corresponding rotatable connector sleeve 218, 220, 222 of adapter assembly 200. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter assembly 200.

The mating of drive connectors 118, 120, 122 of surgical instrument 100 with connector sleeves 218, 220, 222 of adapter assembly 200 allows rotational forces to be independently transmitted via each of the three respective connector interfaces. The drive connectors 118, 120, 122 of surgical instrument 100 are configured to be independently rotated by drive mechanism 160. In this regard, the function selection module 163 of drive mechanism 160 selects which drive connector or connectors 118, 120, 122 of surgical instrument 100 is to be driven by the input drive component 165 of drive mechanism 160.

Since each of drive connectors 118, 120, 122 of surgical instrument 100 has a keyed and/or substantially non-rotatable interface with respective connector sleeves 218, 220, 222 of adapter assembly 200, when adapter assembly 200 is coupled to surgical instrument 100, rotational force(s) are selectively transferred from drive mechanism 160 of surgical instrument 100 to adapter assembly 200.

The selective rotation of drive connector(s) 118, 120 and/or 122 of surgical instrument 100 allows surgical instrument 100 to selectively actuate different functions of end effector 300. As discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 about an articulation axis "Z-Z" that is transverse to longitudinal axis "X-X" (FIG. 2) in direction "A" or "B". In particular, the end effector 300 defines a second longitudinal axis "Y-Y" and is movable from a first position in which the second longitudinal axis "Y-Y" is substantially aligned with the first longitudinal axis "X-X" to at least a second position in which the second longitudinal axis "Y-Y" is disposed at a non-zero angle with respect to the first longitudinal axis "X-X." Additionally, the selective and independent rotation of third drive connector 122 of surgical instrument 100 corresponds to the selective and independent rotation of end effector 300 about longitudinal axis "X-X" (FIG. 2) relative to handle housing 102 of surgical instrument 100 in direction "C" or "D".

As illustrated in FIGS. 1-3 and FIG. 9, handle housing 102 supports a control assembly 103 on a distal surface or side of intermediate housing portion 108. Control assembly 103, in cooperation with intermediate housing portion 108, supports a pair of finger-actuated control buttons 124, 126 and rocker devices 128, 130. In particular, control assembly 103 defines an upper aperture 124a for slidably receiving a first control button 124, and a lower aperture 126a for slidably receiving a second control button 126.

Each one of the control buttons 124, 126 and rocker devices 128, 130 includes a respective magnet (not shown) that is moved by the actuation of an operator. In addition, circuit board 150 includes, for each one of the control buttons 124, 126 and rocker devices 128, 130, respective Hall-effect switches 150a-150d (FIG. 7) that are actuated by the movement of the magnets in the control buttons 124, 126 and rocker devices 128, 130. In particular, located immediately proximal to the control button 124 is a first Hall-effect switch 150a (FIGS. 3 and 7) that is actuated upon the movement of a magnet within the control button 124 upon the operator actuating control button 124. The actuation of first Hall-effect switch 150a, corresponding to control button 124, causes circuit board 150 to provide appropriate signals to function selection module 163 and input drive component 165 of the drive mechanism 160 to close a tool assembly 304 of end effector 300 and/or to fire a stapling/cutting cartridge within tool assembly 304 of end effector 300.

Also, located immediately proximal to rocker device 128 is a second Hall-effect switch 150b (FIGS. 3 and 7) that is actuated upon the movement of a magnet (not shown) within rocker device 128 upon the operator actuating rocker device 128. The actuation of second Hall-effect switch 150b, corresponding to rocker device 128, causes circuit board 150 to provide appropriate signals to function selection module 163 and input drive component 165 of drive mechanism 160 to articulate tool assembly 304 relative to body portion 302 of end effector 300. Advantageously, movement of rocker device 128 in a first direction causes tool assembly 304 to articulate relative to body portion 302 in a first direction, while movement of rocker device 128 in an opposite, e.g., second, direction causes tool assembly 304 to articulate relative to body portion 302 in an opposite, e.g., second, direction.

Furthermore, located immediately proximal to control button 126 is a third Hall-effect switch 150c (FIGS. 3 and 7) that is actuated upon the movement of a magnet (not shown) within control button 126 upon the operator actuating control button 126. The actuation of third Hall-effect switch 150c, corresponding to control button 126, causes circuit board 150 to provide appropriate signals to function selection module 163 and input drive component 165 of drive mechanism 160 to open tool assembly 304 of end effector 300.

In addition, located immediately proximal to rocker device 130 is a fourth Hall-effect switch 150d (FIGS. 3 and 7) that is actuated upon the movement of a magnet (not shown) within rocker device 130 upon the operator actuating rocker device 130. The actuation of fourth Hall-effect switch 150d, corresponding to rocker device 130, causes circuit board 150 to provide appropriate signals to function selection module 163 and input drive component 165 of drive mechanism 160 to rotate end effector 300 relative to handle housing 102 surgical instrument 100. Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

As seen in FIGS. 1-3, surgical instrument 100 includes a fire button or safety switch 132 supported between intermediate housing portion 108 and upper housing portion, and situated above control assembly 103. In use, tool assembly 304 of end effector 300 is actuated between opened and closed conditions as needed and/or desired. In order to fire end effector 300, to expel fasteners therefrom when tool assembly 304 of end effector 300 is in a closed condition, safety switch 132 is depressed thereby instructing surgical instrument 100 that end effector 300 is ready to expel fasteners therefrom.

As illustrated in FIGS. 1 and 10-20, surgical instrument 100 is configured for selective connection with adapter assembly 200, and, in turn, adapter assembly 200 is configured for selective connection with end effector 300.

Figure 29:
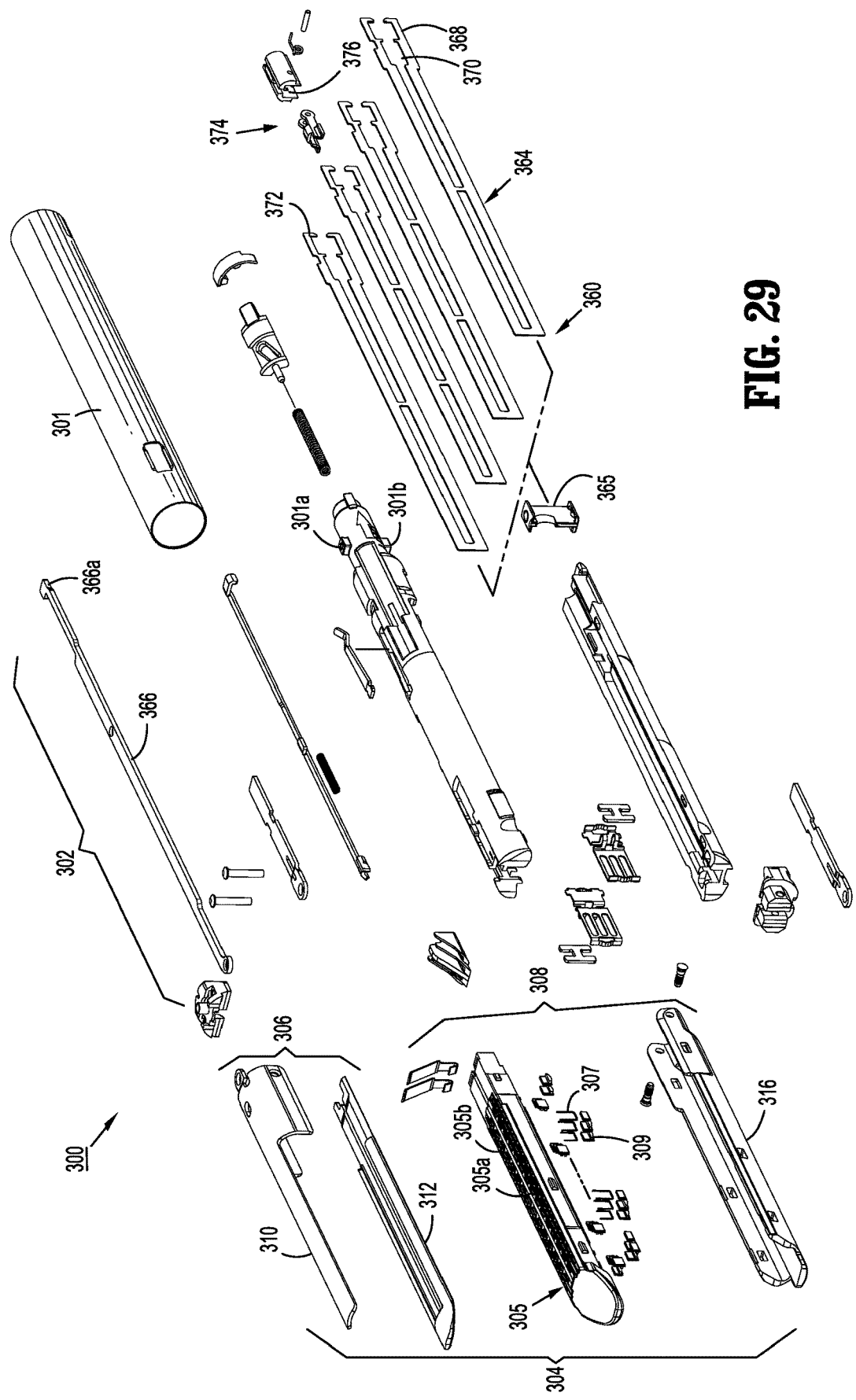
FIG. 29 is an perspective, exploded view of the end effector of FIG. 1, according to the present disclosure.

Adapter assembly 200 is configured to convert a rotation of either of drive connectors 120 and 122 of surgical instrument 100 into axial translation useful for operating a drive assembly 360 and an articulation link 366 of end effector 300, as illustrated in FIG. 29 and discussed in greater detail below.

Adapter assembly 200 includes a first drive transmitting assembly for interconnecting third rotatable drive connector 122 of surgical instrument 100 and a first axially translatable drive member of end effector 300, wherein the first drive transmitting assembly converts and transmits a rotation of third rotatable drive connector 122 of surgical instrument 100 to an axial translation of the first axially translatable drive assembly 360 of end effector 300 for firing.

Adapter assembly 200 includes a second drive transmitting assembly for interconnecting second rotatable drive connector 120 of surgical instrument 100 and a second axially translatable drive member of end effector 300, wherein the second drive transmitting assembly converts and transmits a rotation of second rotatable drive connector 120 of surgical instrument 100 to an axial translation of articulation link 366 of end effector 300 for articulation.

Figure 10:
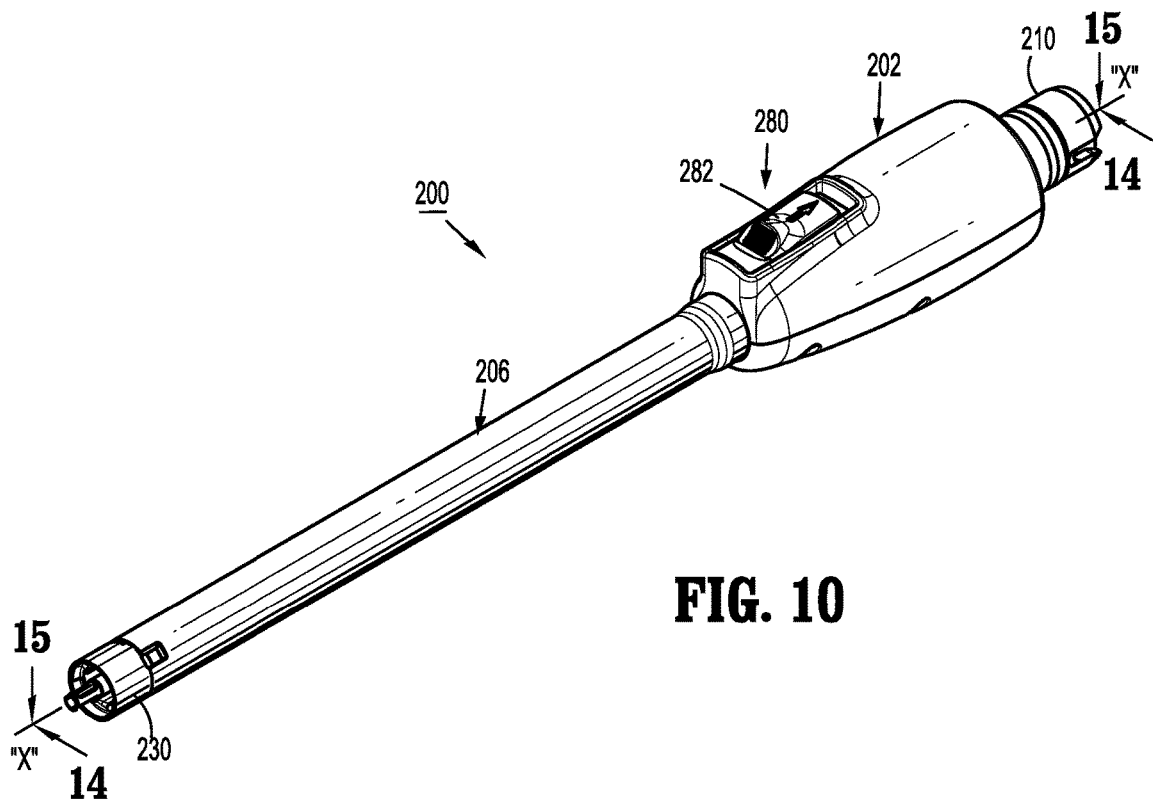
FIG. 10 is a perspective view of the elongated member of FIG. 1, according to the present disclosure.
Figure 11:
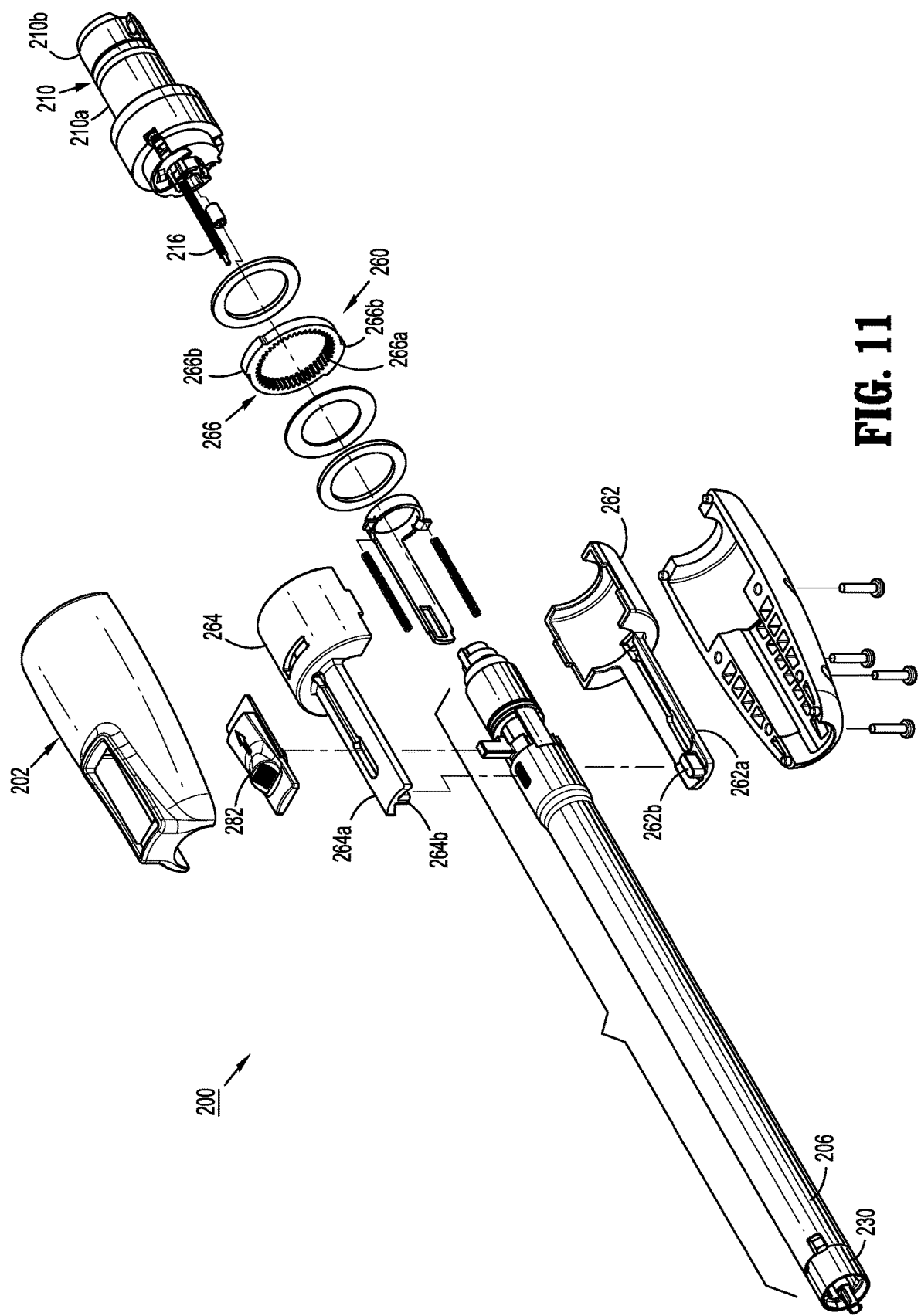
FIG. 11 is a perspective, exploded view of the elongated member of FIG. 1, according to the present disclosure.

With reference to FIGS. 10 and 11, adapter assembly 200 includes a knob housing 202 and an outer tube 206 extending from a distal end of knob housing 202. Knob housing 202 and outer tube 206 are configured and dimensioned to house the components of adapter assembly 200. Outer tube 206 is dimensioned such that outer tube 206 is passable through a typical trocar port, cannula or the like. Knob housing 202 is dimensioned to not enter the trocar port, cannula of the like.

Figure 12:
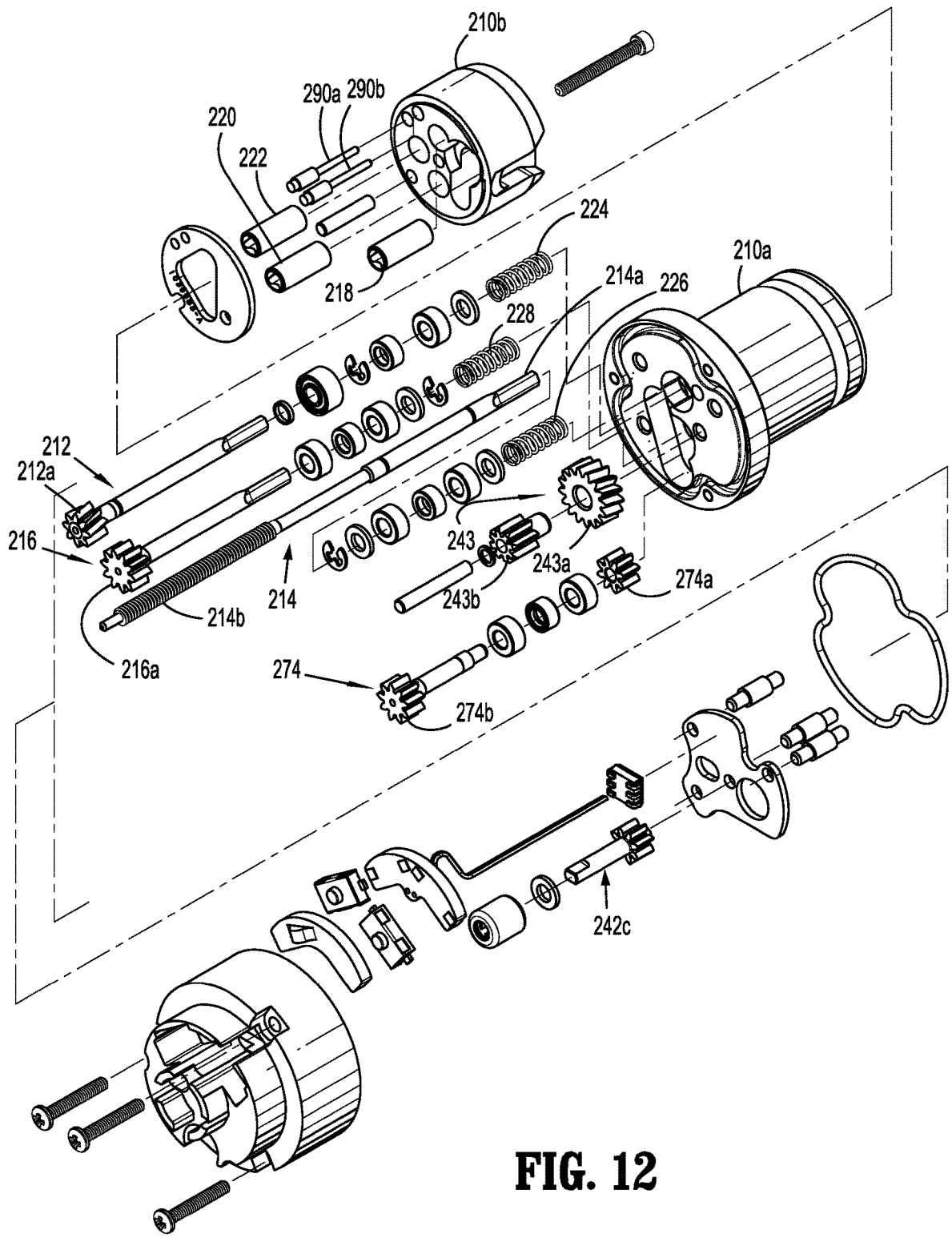
FIG. 12 is a perspective, exploded view of a coupling assembly of the elongated member of FIG. 1, according to the present disclosure.

Knob housing 202 is configured and adapted to connect to connecting portion 108a of upper housing portion 108 of distal half-section 110a of surgical instrument 100. With reference to FIGS. 10-12, adapter assembly 200 includes a surgical device drive coupling assembly 210 at a proximal end thereof and to an end effector coupling assembly 230 at a distal end thereof. Drive coupling assembly 210 includes a distal drive coupling housing 210a and a proximal drive coupling housing 210b rotatably supported, at least partially, in knob housing 202. Drive coupling assembly 210 rotatably supports a first rotatable proximal drive shaft 212, a second rotatable proximal drive shaft 214, and a third rotatable proximal drive shaft 216 therein.

Proximal drive coupling housing 210b is configured to rotatably support first, second and third connector sleeves 218, 220 and 222, respectively. Each of connector sleeves 218, 220, 222 is configured to mate with respective first, second and third drive connectors 118, 120, 122 of surgical instrument 100, as described above. Each of connector sleeves 218, 220, 222 is further configured to mate with a proximal end of respective first, second and third proximal drive shafts 212, 214, 216.

Proximal drive coupling assembly 210 includes a first, a second and a third biasing member 224, 226 and 228 disposed distally of respective first, second and third connector sleeves 218, 220, 222. Each of biasing members 224, 226 and 228 is disposed about respective first, second and third rotatable proximal drive shaft 212, 214 and 216. Biasing members 224, 226 and 228 act on respective connector sleeves 218, 220 and 222 to help maintain connector sleeves 218, 220 and 222 engaged with the distal end of respective drive rotatable drive connectors 118, 120, 122 of surgical instrument 100 when adapter assembly 200 is connected to surgical instrument 100.

In particular, first, second and third biasing members 224, 226 and 228 bias respective connector sleeves 218, 220 and 222 in a proximal direction. In this manner, during assembly of adapter assembly 200 to surgical instrument 100, if first, second and or third connector sleeves 218, 220 and/or 222 is/are misaligned with the drive connectors 118, 120, 122 of surgical instrument 100, first, second and/or third biasing member(s) 224, 226 and/or 228 are compressed. Thus, when drive mechanism 160 of surgical instrument 100 is engaged, drive connectors 118, 120, 122 of surgical instrument 100 will rotate and first, second and/or third biasing member(s) 224, 226 and/or 228 will cause respective first, second and/or third connector sleeve(s) 218, 220 and/or 222 to slide back proximally, effectively coupling drive connectors 118, 120, 122 of surgical instrument 100 to first, second and/or third proximal drive shaft(s) 212, 214 and 216 of proximal drive coupling assembly 210.

Upon calibration of surgical instrument 100, each of drive connectors 118, 120, 122 of surgical instrument 100 is rotated and biasing of connector sleeve(s) 218, 220 and 222 properly seats connector sleeve(s) 218, 220 and 222 over the respective drive connectors 118, 120, 122 of surgical instrument 100 when the proper alignment is reached.

Adapter assembly 200 includes a first, a second and a third drive transmitting assembly 240, 250, 260, respectively, disposed within handle housing 202 and outer tube 206. Each drive transmitting assembly 240, 250, 260 is configured and adapted to transmit or convert a rotation of a first, second and third drive connector 118, 120, 122 of surgical instrument 100 into axial translation of drive tube 246 and drive bar 258 of adapter assembly 200, to effectuate closing, opening, articulating and firing of end effector 300; or a rotation of ring gear 266 of adapter assembly 200, to effectuate rotation of adapter assembly 200.

As shown in FIGS. 13-19, first drive transmitting assembly 240 includes a first distal drive shaft 242 rotatably supported within housing 202 and outer tube 206. A proximal end portion 242a of first distal drive shaft 242 is keyed to a spur gear 242c which is configured for connection to a spur gear 212a keyed to first rotatable proximal drive shaft 212, via a compound gear 243. First distal drive shaft 242 further includes a distal end portion 242b having a threaded outer profile or surface.

First drive transmitting assembly 240 further includes a drive coupling nut 244 rotatably coupled to threaded distal end portion 242b of first distal drive shaft 242, and which is slidably disposed within outer tube 206. Drive coupling nut 244 is keyed to an inner housing tube 206a of outer tube 206 so as to be prevented from rotation as first distal drive shaft 242 is rotated. In this manner, as first distal drive shaft 242 is rotated, drive coupling nut 244 is translated through and/or along inner housing tube 206a of outer tube 206.

First drive transmitting assembly 240 further includes a drive tube 246 surrounding first distal drive shaft 242 and having a proximal end portion connected to drive coupling nut 244 and a distal end portion extending beyond a distal end of first distal drive shaft 242. The distal end portion of drive tube 246 supports a connection member 247 (FIG. 13) configured and dimensioned for selective engagement with drive member 374 of drive assembly 360 of end effector 300.

In operation, as first rotatable proximal drive shaft 212 is rotated, due to a rotation of first connector sleeve 218, as a result of the rotation of the first respective drive connector 118 of surgical instrument 100, spur gear 212a of first rotatable proximal drive shaft 212 engages first gear 243a of compound gear 243 causing compound gear 243 to rotate. As compound gear 243 rotates, a second gear 243b of compound gear 243 is rotated and thus causes spur gear 242c that is keyed to first distal drive shaft 242, that is engaged therewith, to also rotate thereby causing first distal drive shaft 242 to rotate. As first distal drive shaft 242 is rotated, drive coupling nut 244 is caused to be translated axially along first distal drive shaft 242.

As drive coupling nut 244 is caused to be translated axially along first distal drive shaft 242, drive tube 246 is caused to be translated axially relative to inner housing tube 206a of outer tube 206. As drive tube 246 is translated axially, with connection member 247 connected thereto and connected to a drive member 374 of drive assembly 360 of end effector 300, drive tube 246 causes concomitant axial translation of drive member 374 of end effector 300 to effectuate a closure of tool assembly 304 and a firing of tool assembly 304 of end effector 300.

With reference to FIGS. 13-19, second drive transmitting assembly 250 of adapter assembly 200 includes second rotatable proximal drive shaft 214 rotatably supported within drive coupling assembly 210. Second rotatable proximal drive shaft 214 includes a non-circular or shaped proximal end portion 214a configured for connection with second connector 220 which is connected to respective second connector 120 of surgical instrument 100. Second rotatable proximal drive shaft 214 further includes a distal end portion 214b having a threaded outer profile or surface.

Figure 20:
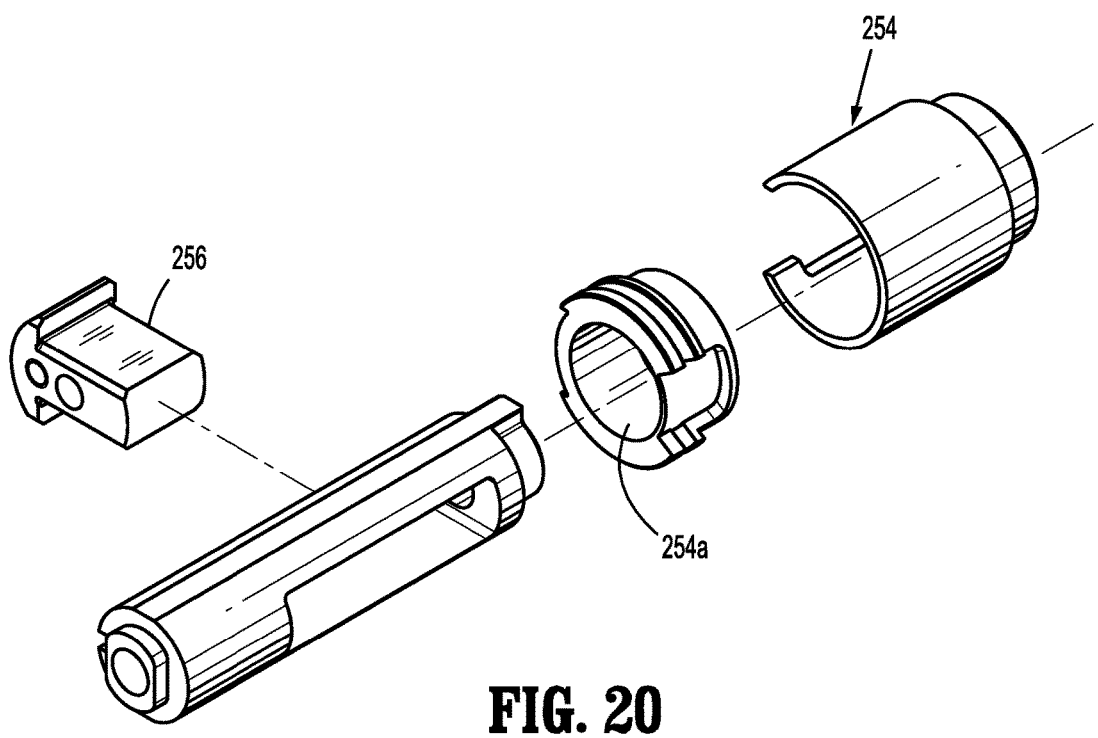
FIG. 20 is a perspective, exploded view of a drive transmitting assembly of the elongated member of FIG. 1, according to the present disclosure.

As illustrated in FIG. 20, second drive transmitting assembly 250 further includes a coupling cuff 254 rotatably and translatably supported within an annular race or recess formed in knob housing 202. Coupling cuff 254 defines a lumen 254a therethrough, and an annular race or recess formed in a surface of lumen 254a. Second drive transmitting assembly 250 further includes a coupling slider 256 extending across lumen 254a of coupling cuff 254 and slidably disposed within the race of coupling cuff 254. Coupling slider 256 is threadably connected to threaded distal end portion 214b of second rotatable proximal drive shaft 214. As so configured, coupling cuff 254 can rotate about second rotatable proximal drive shaft 214, thereby maintaining a radial position of second rotatable proximal drive shaft 214 relative to first rotatable proximal drive shaft 242.

Second rotatable proximal drive shaft 214 defines an axis of rotation, and coupling cuff 254 defines an axis of rotation that is spaced a radial distance from the axis of rotation of second rotatable proximal drive shaft 214. Coupling slider 256 defines an axis of rotation that is coincident with the axis of rotation of coupling cuff 254.

Second drive transmitting assembly 250 further includes a drive bar 258 translatably supported for axial translation through outer tube 206. Drive bar 258 includes a proximal end portion 258a coupled to coupling cuff 254, and a distal end portion 258b defining a coupling hook 258c configured and dimensioned for selective engagement with hooked proximal end 366a of articulation link 366 of end effector 300 (FIG. 29).

In operation, as illustrated in FIGS. 10-19, as drive shaft 214 is rotated due to a rotation of second connector sleeve 220, as a result of the rotation of the second drive connector 120 of surgical instrument 100, coupling slider 256 is caused to be translated axially along threaded distal portion 214b of second rotatable proximal drive shaft 214, which in turn causes coupling cuff 254 to be translated axially relative to knob housing 202. As coupling cuff 254 is translated axially, drive bar 258 is caused to be translated axially. Accordingly, as drive bar 258 is translated axially, with hook 258c thereof connected to hooked proximal end 366a of articulation link 366 of end effector 300 (FIG. 29), drive bar 258 causes concomitant axial translation of articulation link 366 of end effector 300 to effectuate an articulation of tool assembly 304.

As seen in FIGS. 10-19, adapter assembly 200 includes a third drive transmitting assembly 260 supported in knob housing 202. Third drive transmitting assembly 260 includes first and second rotation housing half-sections 262, 264 rotatably supported in knob housing 202, respectively, and an internal rotation ring gear 266 supported and interposed between first and second rotation housing half-sections 262, 264. Each of first and second rotation housing half-sections 262, 264 includes an arm 262a, 264b extending distally therefrom and which are parallel to one another and spaced a transverse distance from one another. Each arm 262a, 264a includes a boss 262b, 264b extending radially inward near a distal end thereof.

Third drive transmitting assembly 260 further includes a pair of rotation transmitting bars 268, 270, each, connected at a proximal end thereof to bosses 262b, 264b of arms 262a, 264a, and at a distal end thereof to a distal coupling assembly 230 supported at a distal end of outer tube 206.

Third drive transmitting assembly 260 includes a ring gear 266 defining an internal array of gear teeth 266a. Ring gear 266 includes a pair of diametrically opposed, radially extending protrusions 266b projecting form an outer edge thereof. Protrusions 266b are disposed within recesses 262c, 264c defined in an inner surface of first and second rotation housing half-sections 262, 264, such that rotation of ring gear 266 results in rotation of first and second rotation housing half-sections 262, 264.

Third drive transmitting assembly 260 further includes third rotatable proximal drive shaft 216 rotatably supported within housing 202 and outer tube 206. A proximal end portion of third rotatable proximal drive shaft 216 is keyed to third connector 222 of adapter assembly 200. Third rotatable proximal drive shaft 216 includes a spur gear 216a keyed to a distal end thereof. A gear set 274 inter-engages spur gear 216a of third rotatable proximal drive shaft 216 to gear teeth 266a of ring gear 266. Gear set 274 includes a first gear 274a engaged with spur gear 216a of third rotatable proximal drive shaft 216, and a second gear 274b engaged with gear teeth 266a of ring gear 266.

In operation, as illustrated in FIGS. 10-19, as third rotatable proximal drive shaft 216 is rotated, due to a rotation of third connector sleeve 222, as a result of the rotation of the third respective drive connector 122 of surgical instrument 100, spur gear 216a of third rotatable proximal drive shaft 216 engages first gear 272a of gear set 274 causing gear set 274 to rotate. As gear set 274 rotates, second gear 274b of gear set 274 is rotated and thus causes ring gear 266 to also rotate thereby causing first and second rotation housing half-sections 262, 264 to rotate. As first and second rotation housing half-sections 262, 264 are rotated, rotation transmitting bars 268, 270, and distal coupling assembly 230 connected thereto, are caused to be rotated about longitudinal axis "X-X" of adapter assembly 200 (FIG. 10). As distal coupling 230 is rotated, end effector 300, that is connected to distal coupling assembly 230, is also caused to be rotated about a longitudinal axis of adapter assembly 200.

With reference to FIGS. 10, 11, 13 and 18, adapter assembly 200 further includes a lock mechanism 280 for fixing the axial position and radial orientation of drive tube 246 for the connection and disconnection of end effector 300 thereto. Lock mechanism 280 includes a release button 282 slidably supported on knob housing 202. Release button 282 is connected to an actuation bar 284 that extends longitudinally through outer tube 206. Actuation bar 284 is interposed between outer tube 206 and inner housing tube 206a and distal tip housing 289. Actuation bar 284 moves in response to the insertion of end effector 300 and/or movement of lock release button 282. The tip housing 289 is configured and dimensioned for insertion of end effector 300 thereinto.

The tip housing 289 includes a bayonet connection mount 291 for releasably connecting to the end effector 300. With reference to FIG. 29, the end effector 300 includes a pair of lugs 301a and 301b disposed at a proximal portion of the end effector 300. The lugs 301a and 301b are configured and dimensioned to be inserted into the bayonet connection mount 291 having a pair of corresponding bayonet channels.

Figure 13:
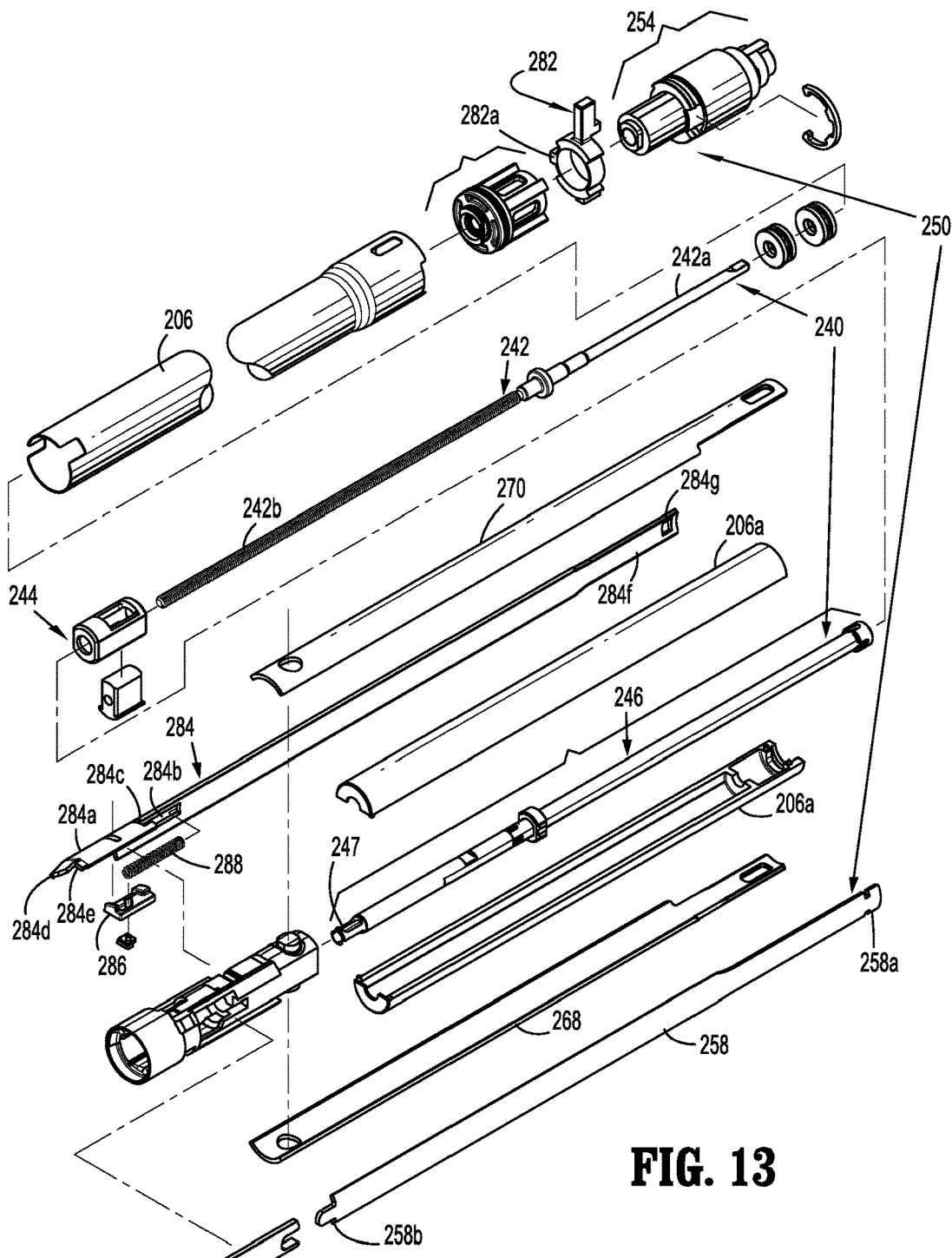
FIG. 13 is a perspective, exploded view of a drive transmitting assembly of the elongated member of FIG. 1, according to the present disclosure.
Figure 14:
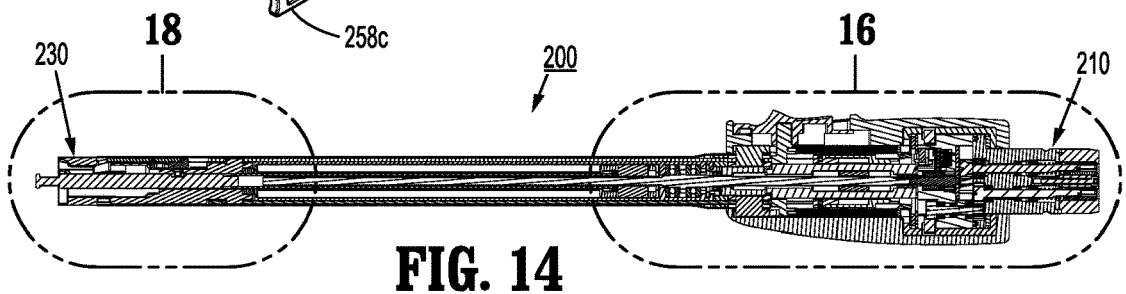
FIG. 14 is a side, cross-sectional view of the elongated member of FIG. 1, according to the present disclosure.
Figure 15:
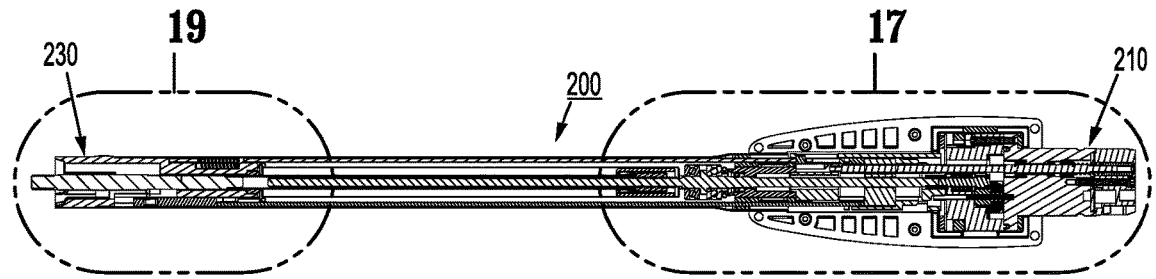
FIG. 15 is a top, cross-sectional view of the elongated member of FIG. 1, according to the present disclosure.
Figure 16:
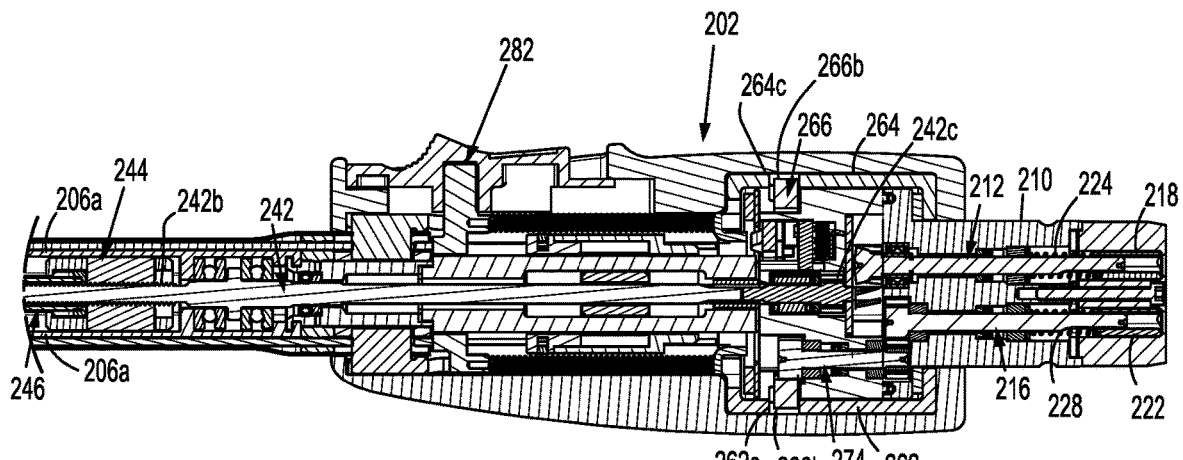
FIG. 16 is an enlarged, side, cross-sectional view of a proximal area of detail of the elongated member of FIG. 1, according to the present disclosure.
Figure 17:
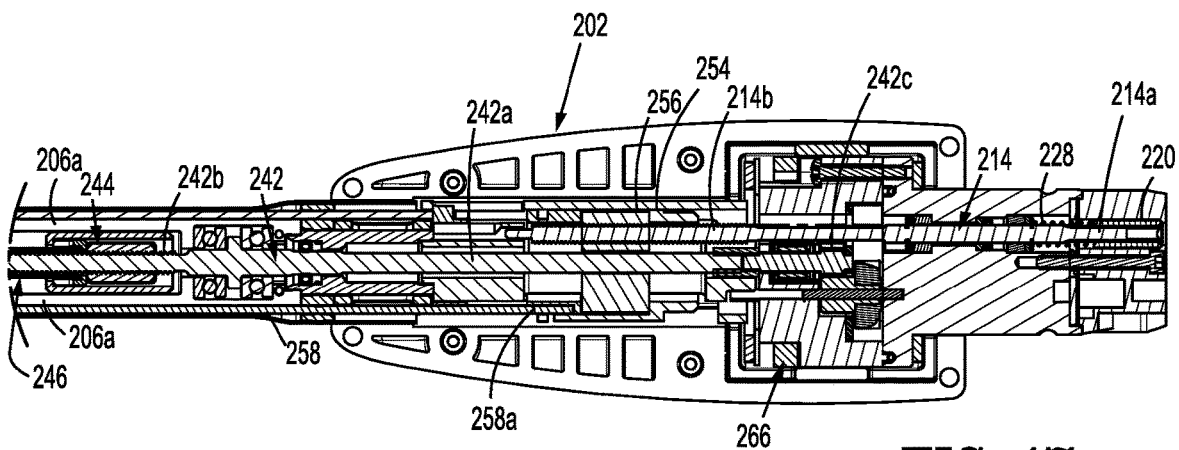
FIG. 17 is an enlarged, top, cross-sectional view of the proximal area of detail of the elongated member of FIG. 1, according to the present disclosure.
Figure 21:
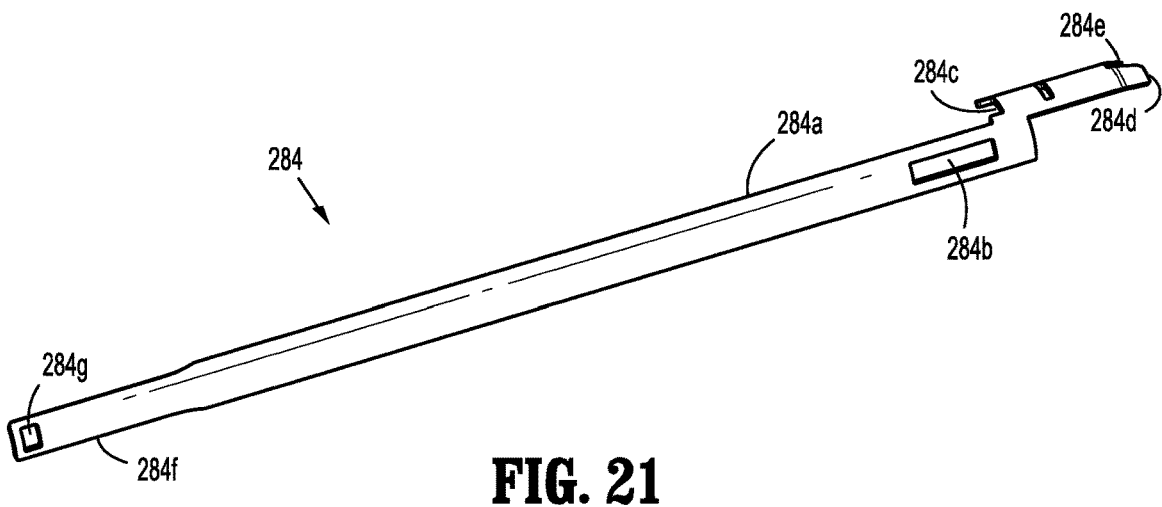
FIG. 21 is a perspective view of an actuation bar of the elongated member of FIG. 1, according to the present disclosure.
Figure 22:
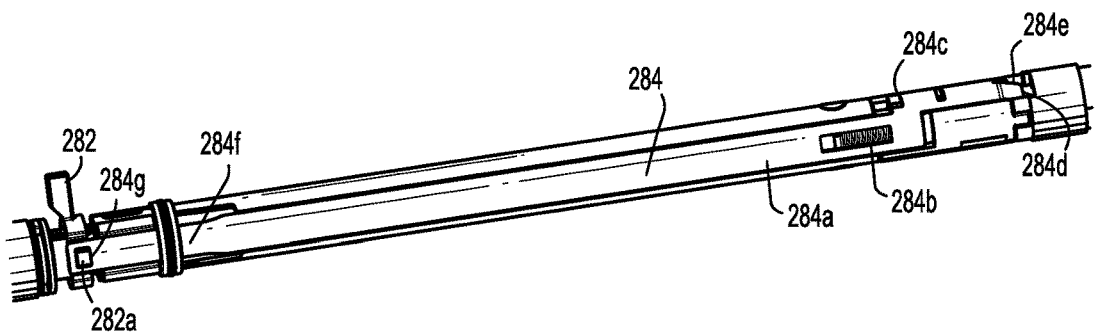
FIG. 22 is a perspective, partially-disassembled view of the elongated member of FIG. 1, according to the present disclosure.

With reference to FIG. 13 and FIGS. 21 and 22, actuation bar 284 includes a distal portion 284a defining a window 284b, and a finger extending distally from distal portion 284a. The finger of actuation bar 284 includes a proximal cam surface 284c and a distal large tab 284d and a distal small tab 284e. The actuation bar 284 further includes a proximal portion 284f having an opening 284g configured and dimensioned to engage a tab 282a of the release button 282.

Figure 23:
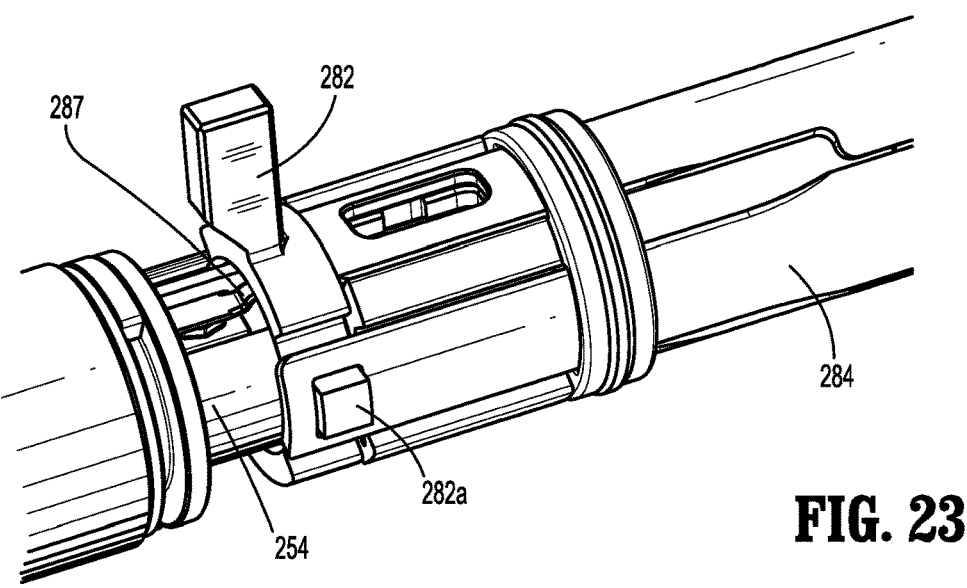
FIG. 23 is an enlarged, perspective, partially-disassembled view of a proximal portion of the elongated member of FIG. 1 in an unloaded configuration, according to the present disclosure.

With reference to FIG. 13 and FIG. 23, the lock mechanism 280 further includes a leaf spring sensor 287 disposed at the distal end of the coupling cuff 254 and underneath the release button 282, such that longitudinal travel of the release button 282 in the proximal direction engages the sensor 287 as the release button 282 travels in either a proximal or distal direction therealong.

Figure 18:
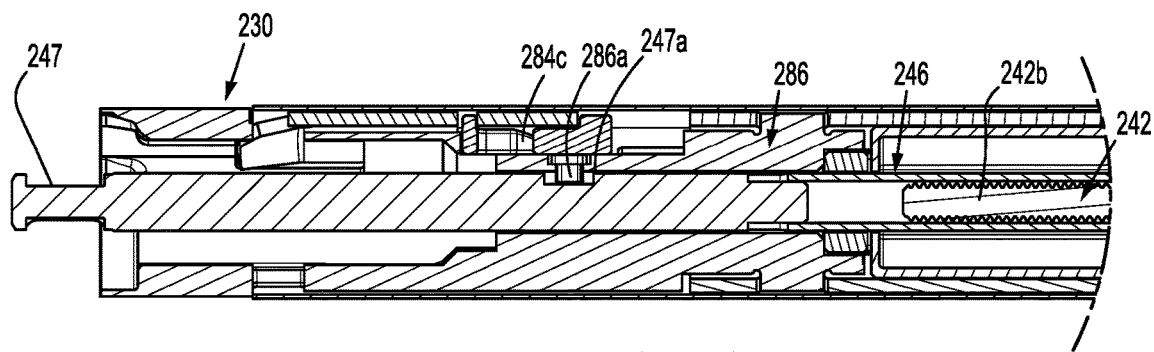
FIG. 18 is an enlarged, side, cross-sectional view of a distal area of detail of the elongated member of FIG. 1, according to the present disclosure.
Figure 19:
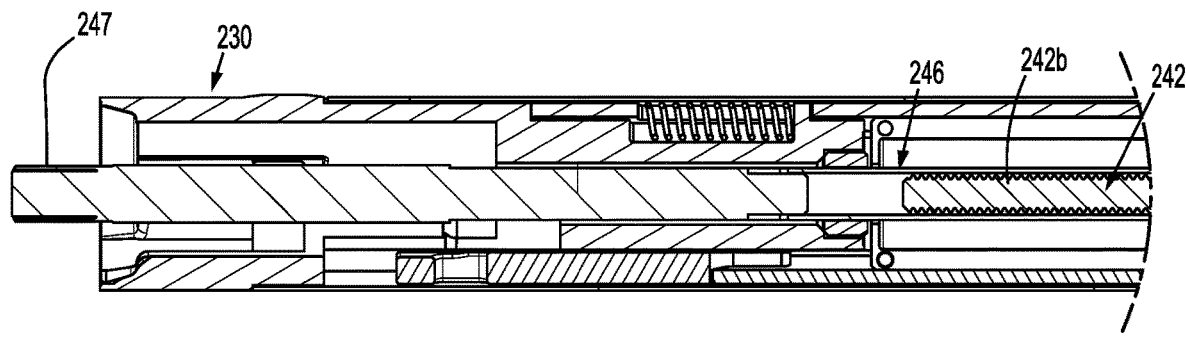
FIG. 19 is an enlarged, top, cross-sectional view of the distal area of detail of the elongated member of FIG. 1, according to the present disclosure.

As illustrated in FIGS. 13 and 18, lock mechanism 280 further includes a lock out 286 supported on distal coupling assembly 230 at a location in registration with window 284b of distal portion 284a of actuation bar 284. Lock out 286 includes a tab 286a extending toward connection member 247 of drive tube 246. Tab 286a of lock out 286 is configured and dimensioned to selectively engage a cut-out 247a formed in connection member 247 of drive tube 246. Lock mechanism 280 further includes a biasing member 288 tending to maintain lock out 286 and tab 286a thereof spaced away from cut-out 247a formed in connection member 247 of drive tube 246.

Figure 24:
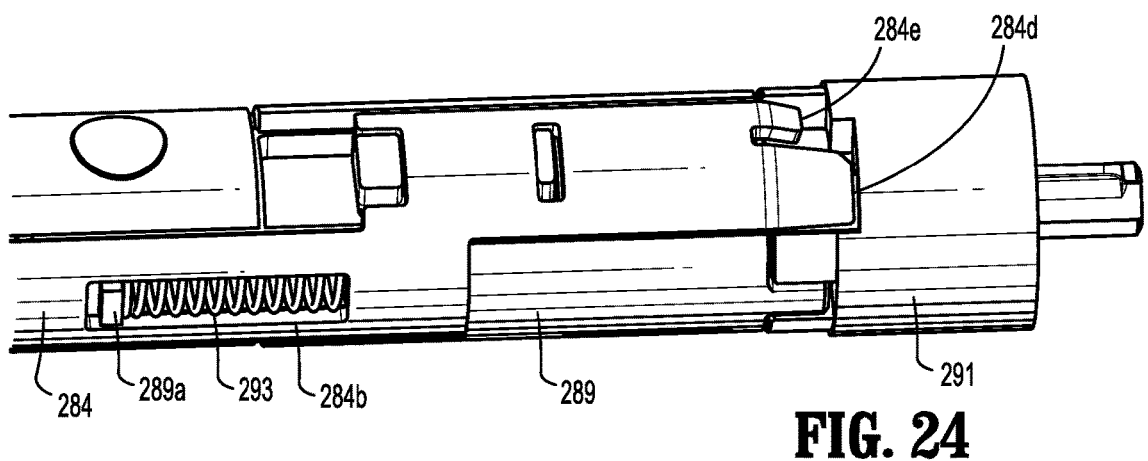
FIG. 24 is an enlarged, perspective, partially-disassembled view of a distal portion of the elongated member of FIG. 1 in the unloaded configuration, according to the present disclosure.

With reference to FIG. 23 and FIG. 24, the lock mechanism 280 is illustrated in its "home" (e.g., unloaded) configuration in which the end effector 300 is not connected to the adapter assembly 200. In this configuration, the actuation bar 284 is extended distally and the distal large tab 284d is in contact with the bayonet connection mount 291. The lock mechanism 280 includes a spring 293 disposed within the window 284b of the actuation bar 284, which biases the actuation bar 284 against a rest or stop 289a of the tip housing 289. Since the actuation bar 284 is extended distally, the release button 282 is also disposed distally of the sensor 287 (FIG. 23), signaling to the surgical instrument 100 that the end effector 300 is not connected to the adapter assembly 200, as described in further detail below.

Figure 25:
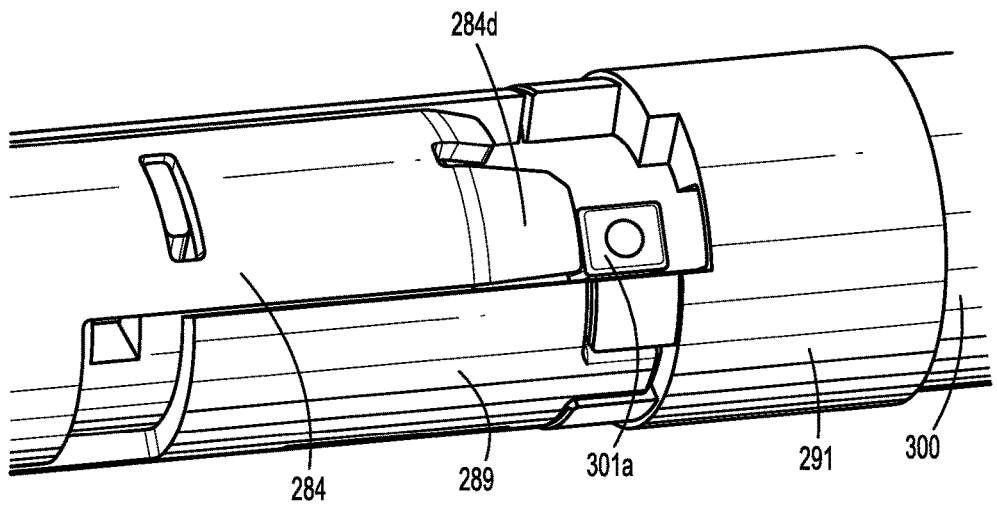
FIG. 25 is an enlarged, perspective, partially-disassembled view of the distal portion of the elongated member of FIG. 1 in a loaded configuration, according to the present disclosure.
Figure 26:
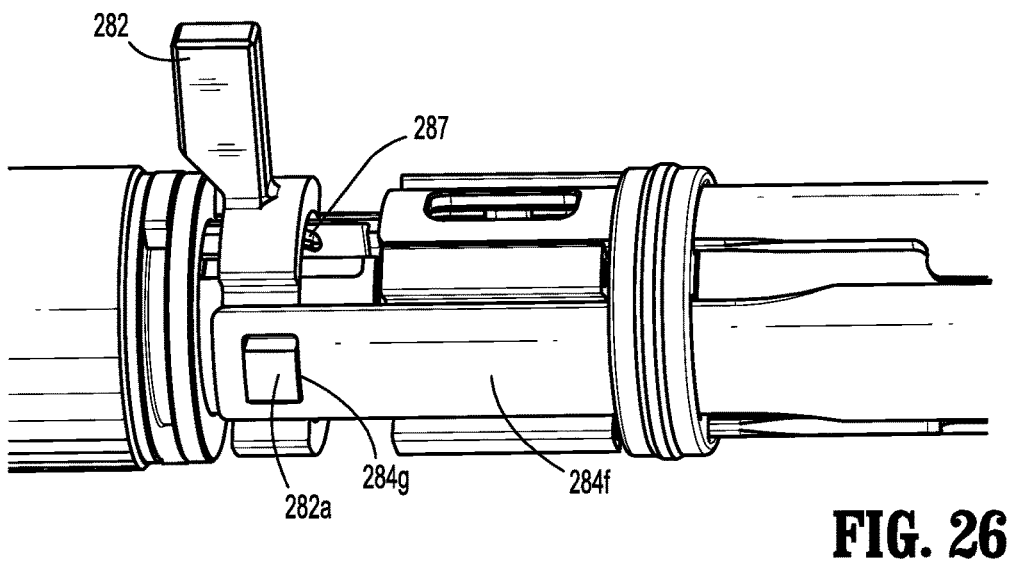
FIG. 26 is an enlarged, perspective, partially-disassembled view of the proximal portion of the elongated member of FIG. 1 in the loaded configuration, according to the present disclosure.

With reference to FIGS. 25 and 26, insertion of the end effector 300 into adapter assembly 200 is illustrated. As the end effector 300 is inserted into the bayonet connection mount 291 of the tip housing 289, the lug 301a engages the distal large tab 284d of the actuation bar 284 pushing it proximally as shown in FIG. 25, below. This in turn, pushes the release button 282 in the proximal direction past the sensor 287, thereby toggling the sensor 287. This signals the surgical instrument 100 that the end effector 300 has been inserted, but not secured, as described in further detail below.

Proximal movement of the actuation bar 284 also locks the position and/or orientation of drive tube 246. In particular, as the actuation bar 284 is moved proximally, the cam surface 284c of actuation bar 284 engages the lock arm 286 and urges lock out 286 toward drive tube 246, against the bias of biasing member 288, such that tab 286a of lock out 286 is received in cut-out 247a formed in connection member 247 of drive tube 246. In this manner, drive tube 246 is prevented from distal and/or proximal movement.

Figure 27:
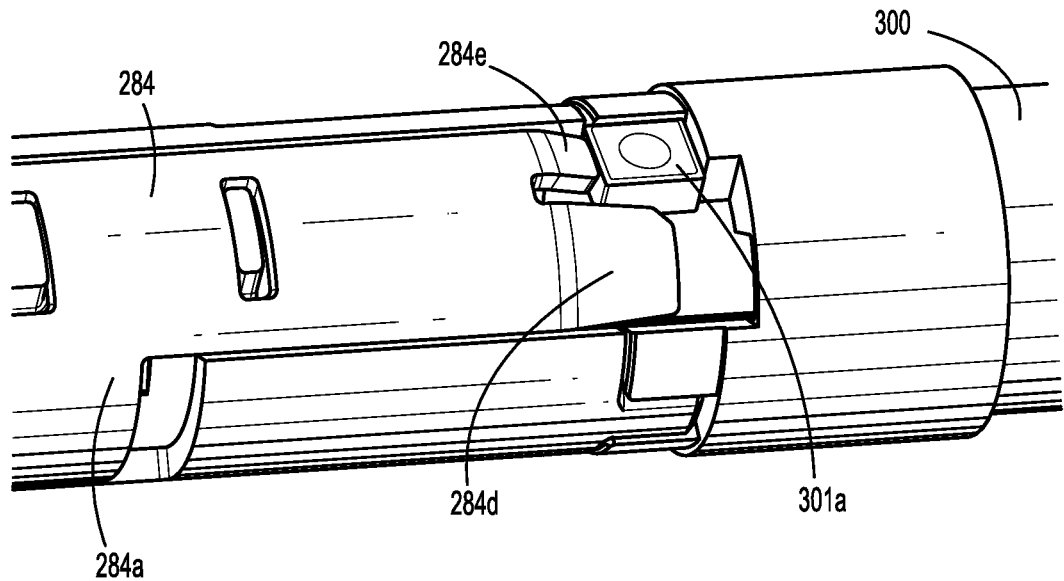
FIG. 27 is an enlarged, perspective, partially-disassembled view of the distal portion of the elongated member of FIG. 1 in a locked configuration, according to the present disclosure.
Figure 28:
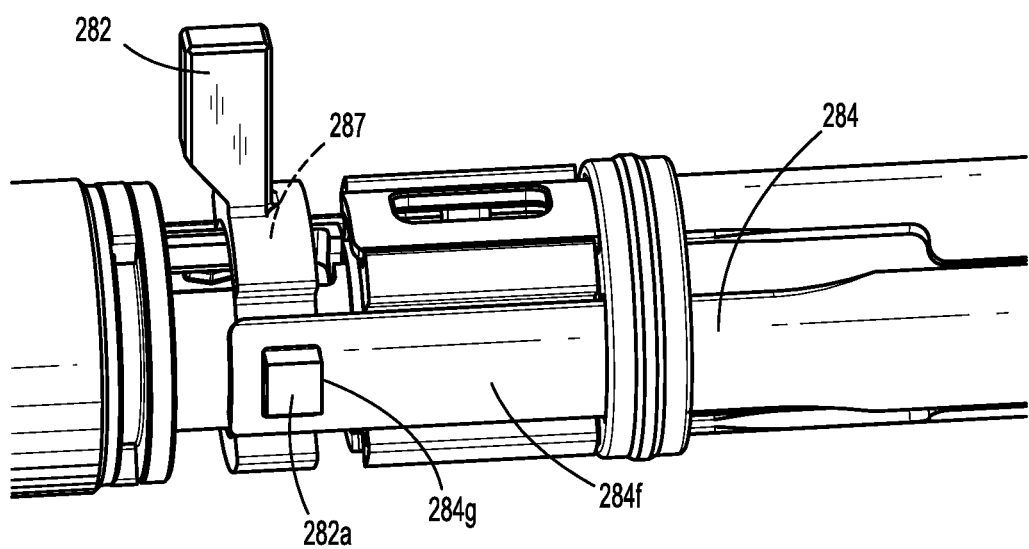
FIG. 28 is an enlarged, perspective, partially-disassembled view of the proximal portion of the elongated member of FIG. 1 in the locked configuration, according to the present disclosure.

With reference to FIGS. 27 and 28, securing of the end effector 300 within the connection mount 291 of adapter assembly 200 is illustrated. After distal insertion of the end effector 300, it is secured to adapter assembly 200 by rotation thereof about the longitudinal axis "X-X." As the end effector 300 is rotated within the bayonet connection mount 291 of the tip housing 289, the lug 301a disengages the distal large tab 284d and engages the distal small tab 284e of the actuation bar 284. This allows the action bar 284 to move distally under the biasing of the spring 293 (see FIG. 24) as shown in FIG. 27, below. The spring 293 retains the actuation bar 284 in the distal direction with the lug 301a disposed between the connection mount 291 and the distal large tab 284d, thereby securing the end effector 300. Distal movement of the actuation bar 284 also allows the distal small tab 284e to rest against the lug 301a, which in turn, moves the release button 282 to rest on the sensor 287, thereby continually engaging the sensor 287 and signaling the surgical instrument 100 that the end effector 300 has been inserted and secured to adapter assembly 200, as described in further detail below.

Distal movement of the actuation bar 284 also allows for disengagement of the drive tube 246 with the end effector 300. In particular, as the actuation bar 284 is moved distally, the cam surface 284c is disengaged from lock out 286 thereby allowing biasing member 288 to urge lock out 286 and tab 286a thereof out of cut-out 247a formed in connection member 247 of drive tube 246.

Disconnection of the end effector 300 may be accomplished by moving the release button 282 in the proximal direction. This also moves the actuation bar 284 in the proximal direction and simultaneously disengages the release button 282 from the sensor 287, thereby signaling the surgical instrument 100 that the end effector 300 has been disengaged. Proximal movement of the actuation bar 284 moves the distal large and small tabs 284d and 284e from engagement with the lug 301a of the end effector 300. While the release button 282 is continuously engaged in the proximal direction, the end effector 300 is rotated and then pulled out from the adapter assembly 200. As the release button 282 is disengaged, the actuation bar 284 is moved in the distal direction by the spring 293 along with the release button 282, which once again toggles the sensor 287 to signal the surgical instrument 100 that the end effector 300 has been removed.

Figure 31:
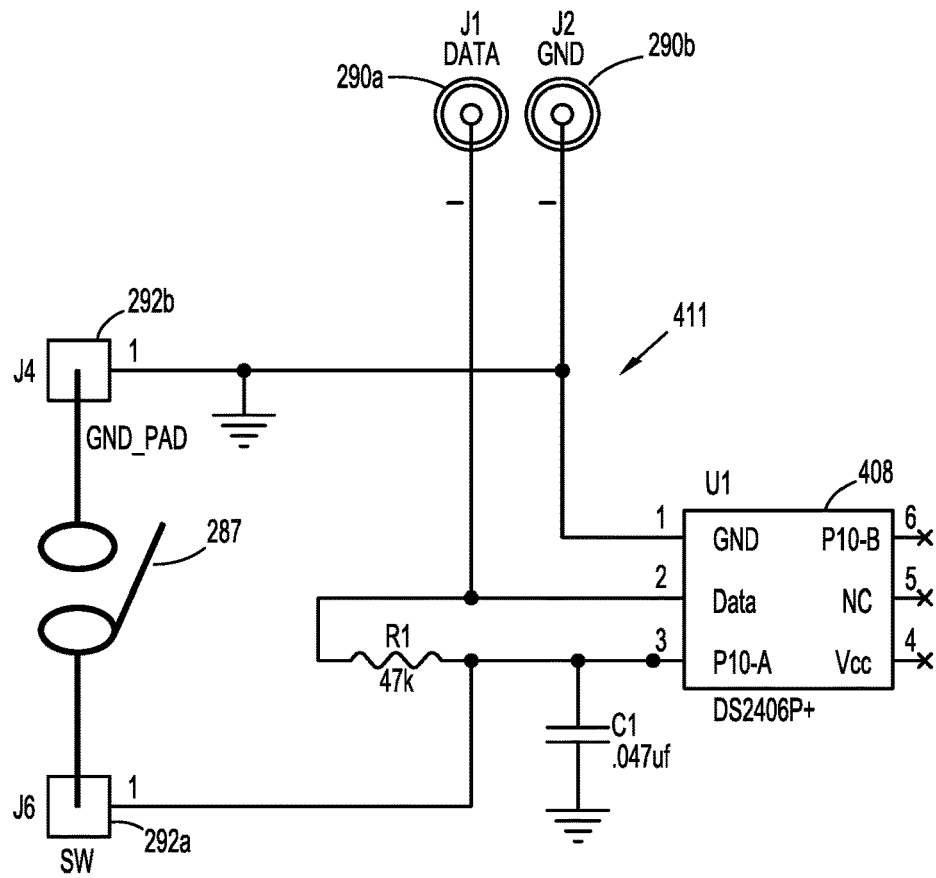
FIG. 31 is a schematic diagram of an end effector detection circuit according to the present disclosure.

As seen in FIGS. 6, 12 and 31, adapter assembly 200 includes a pair of electrical contact pins 290a, 290b for electrical connection to a corresponding electrical plug 190a, 190b disposed in connecting portion 108a of surgical instrument 100. Adapter assembly 200 further includes a circuit board 292 supported in knob housing 202 and which is in electrical communication with electrical contact pins 290a, 290b The circuit board 292 provides the circuit board 150 of surgical instrument 100 with autoclave and usage counts as well as signals from the sensor 287.

With reference to FIG. 29, the end effector 300 includes a proximal body portion 302 and a tool assembly 304. Proximal body portion 302 is releasably attached to a distal coupling 230 of adapter assembly 200 and tool assembly 304 is pivotally attached to a distal end of proximal body portion 302. Tool assembly 304 includes an anvil assembly 306 and a cartridge assembly 308. Cartridge assembly 308 is pivotal in relation to anvil assembly 306 and is movable between an open or unclamped position and a closed or clamped position for insertion through a cannula of a trocar. Proximal body portion 302 includes at least a drive assembly 360 and an articulation link 366.

Referring to FIG. 29, drive assembly 360 includes a flexible drive beam 364 having a distal end which is secured to a dynamic clamping member 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of beam 364. Drive member 374 defines a proximal porthole 376 which receives connection member 247 of drive tube 246 of first drive transmitting assembly 240 of adapter assembly 200 when end effector 300 is attached to distal coupling 230 of adapter assembly 200.

When drive assembly 360 is advanced distally within tool assembly 304, an upper beam of clamping member 365 moves within a channel defined between anvil plate 312 and anvil cover 310 and a lower beam moves over the exterior surface of carrier 316 to close tool assembly 304 and fire staples therefrom.

Proximal body portion 302 of end effector 300 includes an articulation link 366 having a hooked proximal end 366a which extends from a proximal end of end effector 300. Hooked proximal end 366a of articulation link 366 engages coupling hook 258c of drive bar 258 of adapter assembly 200 when end effector 300 is secured to distal housing 232 of adapter assembly 200. When drive bar 258 of adapter assembly 200 is advanced or retracted as described above, articulation link 366 of end effector 300 is advanced or retracted within end effector 300 to pivot tool assembly 304 in relation to a distal end of proximal body portion 302.

As illustrated in FIG. 29, cartridge assembly 308 of tool assembly 304 includes a removable staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of surgical instrument 100, drive assembly 360 abuts an actuation sled and pushes actuation sled through cartridge 305. As the actuation sled moves through cartridge 305, cam wedges of the actuation sled sequentially engage staple pushers 309 to move staple pushers 309 vertically within staple retention slots 305b and sequentially eject a single staple 307 therefrom for formation against anvil plate 312.

Construction and operation of end effector 300 is described in further detail in a commonly-owned U.S. Patent Publication No. 2009/0314821, filed on Aug. 31, 2009, entitled "TOOL ASSEMBLY FOR A SURGICAL STAPLING DEVICE," the entire contents of which are incorporated by reference herein.

Figure 30:
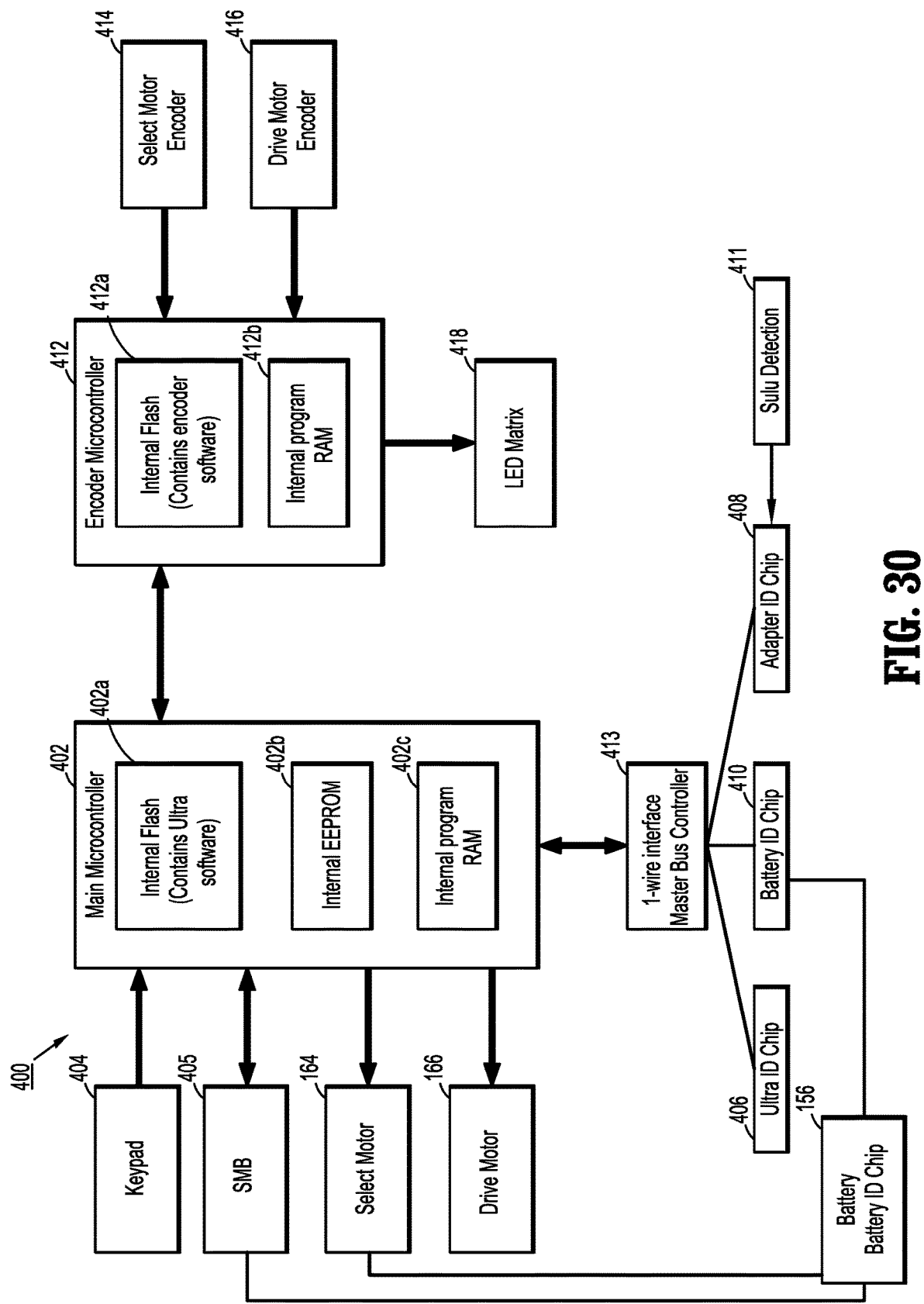
FIG. 30 is schematic hardware diagram of the electromechanical surgical system of FIG. 1, according to the present disclosure.

A high level hardware architectural view of the system 10 is shown in FIG. 30 and illustrates the interconnections between the various hardware and software interfaces. The hardware interface 400 includes a main master microcontroller 402 disposed on the circuit board 154 that handles all of the communications and an encoder microcontroller 412 as the slave, Hall-effect scanning of finger-actuated control buttons 124, 126 and rocker devices 128, 130, communication through a communication interface 413 with ID chips 406, 408, 410, LED flash rate and updating, motor control of the first motor (e.g., select motor) 164 and the second motor (e.g., drive motor) 166, and all other high-level functionality.

The main microcontroller 402 includes an internal flash memory 402a, an internal storage memory 402b, and an internal random access memory (RAM) 402c. The flash memory 402a may be any suitable erasable, rewritable storage suitable for non-volatile storage of computer data and software that can be electrically erased and programmed. The flash memory 402a contains the device software for operating surgical instrument 100, shaft assembly 200 and/or end effector 300. The software stored in the flash memory 402a may be updated via a serial connector disposed in the lower housing portion 104 using a bootloader. The bootloader is an independent program that is also resident in the flash memory 402a and controls the software update process.

The storage memory 402b is used for storing (e.g., reading and writing) a variety of data regarding operation of surgical instrument 100, such as usage counter, calibration presets, event logging, etc. The storage memory 402b may also be any suitable erasable, rewritable storage suitable for non-volatile storage of computer data. RAM 402c is used during execution of the program instructions by the main microcontroller 402, namely the instructions are loaded from the flash memory 402a into the RAM 402c.

The main microcontroller 402 is also coupled to the control assembly 103, namely finger-actuated control buttons 124, 126 and rocker devices 128, 130, and is configured to receive inputs therefrom. The main microcontroller 402 then controls surgical instrument 100, namely, operation of the first motor (e.g., select motor) 164 and the second motor (e.g., drive motor) 166 in response to the inputs and operation software as discussed in further detail below. The main microcontroller 402 is further coupled to a system management bus (SMB) 405 that is used to communicate with the battery 156. In particular, battery status such as temperature and capacity is communicated over the SMB 405.

The main microcontroller 402 also communicates with an Instrument ID chip 406, an adapter ID chip 408, and a battery ID chip 410, disposed in surgical instrument 100, shaft assembly 200, and the battery 156, respectively through a communication interface 413. The interface 413 provides a single-contact communication interface with the main microcontroller 402 and offers electronic identification of reusable components, namely shaft assembly 200, the battery 156, and end effector 300 to prevent these components from being used beyond their specified limit.

The Instrument ID chip 406 identifies surgical instrument 100 and records usage information to confirm on startup that surgical instrument 100 has not reached its autoclave cycle limit and/or handle fire limit. The adapter ID chip 408 identifies the type of shaft assembly 200 and includes an end effector detection circuit 411 for detecting the presence of the end effector 300. The adapter ID chip 408 also records usage information to ensure that shaft assembly 200 has not reached its autoclave cycle limit and/or fire limit. The battery ID chip 410 identifies the battery 156 and records usage information, such as charge cycle count, and is used to prevent operation of surgical instrument 100 with unsupported batteries, batteries not capable of firing the end effector 300 successfully and/or batteries that exceed charge cycle count limits.

The hardware interface 400 also includes an encoder microcontroller 402 also disposed on the circuit board 154 and coupled to the main microcontroller 402. The encoder microcontroller 402 includes an internal flash memory 412a and an internal random access memory (RAM) 412b. The flash memory 412a is used for storage of the software controlling the operation of the encoder microcontroller 402 and off-board components such as motors 164, 166 and illumination member 116. RAM 412b is used during execution of the program instructions by the encoder microcontroller 402, namely the instructions are loaded from the flash memory 412a into the RAM 412c.

Figure 32:
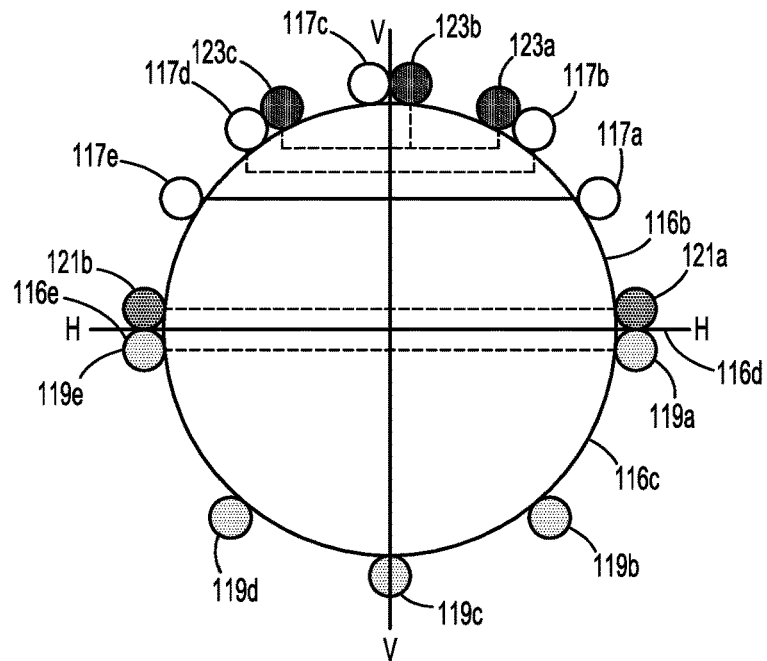
FIG. 32 is a front, schematic view of an illumination member of the surgical instrument of FIG. 1, according to the present disclosure.

The encoder microcontroller 402 is responsible for receiving feedback from a select motor encoder 414 and a drive motor encoder 416. The select and drive motor encoders 414 and 416 are configured to receive feedback from Hall Effect sensors that monitor rotation of the first motor (e.g., select motor) 164 and the second motor (e.g., drive motor) 166 via their respective encoder pulse counters. In particular, the encoder microcontroller 402 counts the motor encoding tick pulses from both the select and drive motors 164 and 166 to attain position and velocity thereof. The encoder microcontroller 402 reports this information to the main microcontroller 402 when requested. The encoder microcontroller 402 is also coupled to the illumination member 116, which is shown in FIG. 32. The illumination member 116 includes a plurality LEDs disposed around a circumference of the illumination member 116.

The software resident in the flash memory 402a is executed by the main microcontroller 402 as surgical instrument 100 is powered up. Upon startup, surgical instrument 100 is initialized, which includes activation of hardware systems disposed on the circuit board, such as I/O ports, analog-to-digital converter, real time clock, motor PW, data monitoring, pulse counter communication, communication, and the watchdog, are activated. In addition, initialization includes testing operation of the microcontrollers 402 and 412 as well as verification of the integrity of the code and data stored in the flash memory 402a, storage memory 402b, and flash memory 412a.

If the initialization is successful, the main microcontroller 402 commences calibration tests of the selector and drive motors 164 and 166. These tests verify the drive electronics of the motors 164 and 166 and calibrate the selector motor 164 to its home position.

The communication interface 413 is also tested to verify that communication is established with the ID chips 406, 408, 410 of surgical instrument 100, shaft assembly 200, and the battery 156.

Battery 156 is also initialized, which includes verifying that the battery 156 is supported based on its ID number. In addition, the following tests are performed: 1) battery capacity is tested at startup and is tested continuously to ensure it is greater than a predetermined threshold prior to firing; 2) the battery temperature is tested continuously to ensure it is in a suitable operational range; and 3) the battery full charge capacity is also tested for end-of-life condition.

The main microcontroller 402 also verifies the number of remaining uses of surgical instrument 100 and shaft assembly 200, e.g., whether the autoclave cycle and handle fire limits have been reached.

If any of the above tests and/or calibrations fails, a corresponding error is annunciated on the illumination member 116 as described in further detail below with respect to FIGS. 32-34D. If all of the above tests have been completed successfully, then a ready status signal is displayed on the illumination member 116.

After surgical instrument 100 is initialized, shaft assembly 200 is also recognized and calibrated. During startup, surgical instrument 100 determines if shaft assembly 200 and/or end effector 300 are connected. When connected, the end effector 300 is automatically retracted to the full open position and shaft assembly 200 is not calibrated until end effector 300 is removed.

After startup, surgical instrument 100 monitors the communication interface 413 (e.g., at a rate of 1 hertz) for the presence of an attached shaft assembly 200. In particular, the main microcontroller 402 interrogates the ID chip 408 of shaft assembly 200 to determine if it is a supported shaft assembly 200. If the attached adapted is unsupported and/or unknown, calibration does not occur and a corresponding error is displayed on the illumination member 116.

Shaft assembly 200 is calibrated without end effector 300 being attached. An articulation range of shaft assembly 200 is calibrated to obtain a reference position by driving the drive shaft 214 left until it stops at its mechanical limit. Once left end stop is detected, drive shaft 214 is driven right to center position. The clamping drive shaft 212 is calibrated by obtaining a reference position by driving the drive shaft 212 proximally until it stops at its mechanical limit. Once end stop is detected, drive shaft 212 is driven distally to home position. If articulation or rotation calibration fail, no further operation is possible until shaft assembly 200 has been removed.

After startup, surgical instrument 100 monitors the communication interface 413 (e.g., at a rate of 1 hertz) for the presence of an attached end effector 300, such that when end effector 300 is removed and motor movement has occurred since last calibration, surgical instrument 100 will require recalibration of shaft assembly 200.

In embodiments, the end effector 300 and/or the staple cartridge 305 may be replaced. In particular, the communication interface 413 (e.g., at a rate of 1 hertz) monitors for removal and reattachment of the end effector 300. If it is detected that the end effector 300 and/or the staple cartridge 305 have been replaced the surgical instrument 100 is recalibrated by fully opening and then closing of the anvil assembly 306 and the cartridge assembly 308 of end effector 300.

Figure 9:
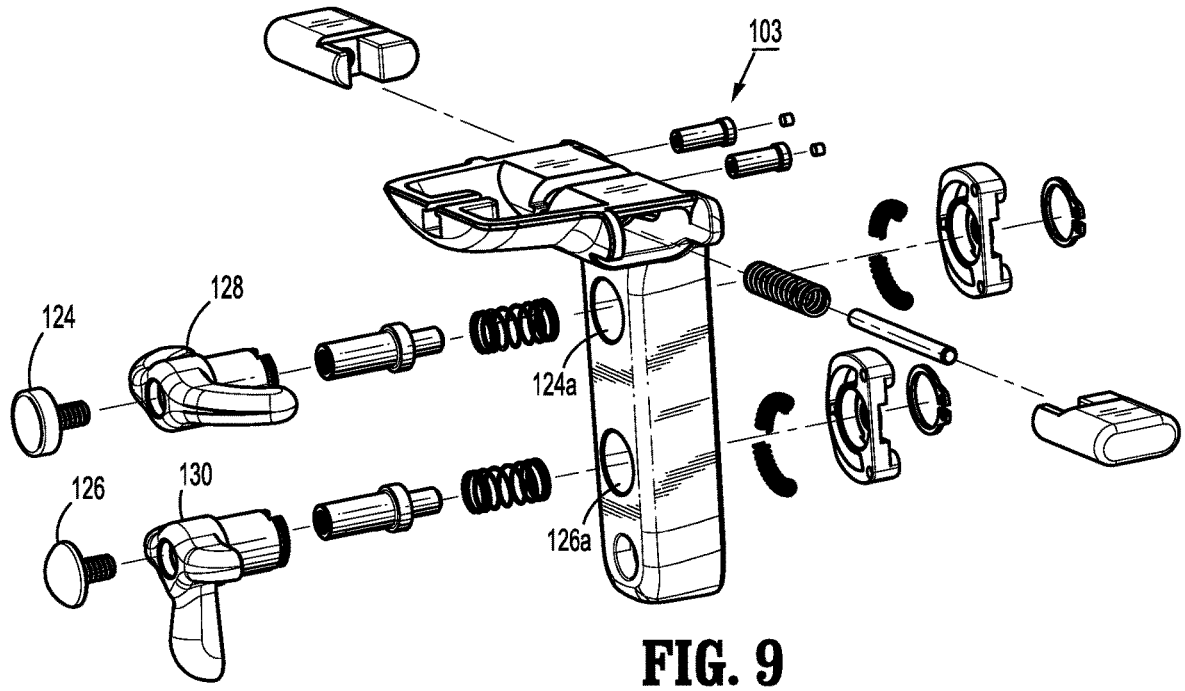
FIG. 9 is a perspective, exploded view of a control assembly of the surgical instrument of FIG. 1, according to the present disclosure.

After it is determined that all of the components are verified and calibrated, surgical instrument 100 is ready for use. With reference to FIG. 9, the control button 124 is actuated to effect clamping and/or firing of end effector 300. The control button 126 is used to effect opening of the anvil assembly 306 and the cartridge assembly 308 of end effector 300. The rocker switch 128 is used to articulate the tool assembly 304 relative to body portion 302 of end effector 300. The rocker switch 130 is used to rotate end effector 300 and shaft assembly 200 relative to surgical instrument 100 about the longitudinal axis "X-X." The safety switch 132 is used to signal surgical instrument 100 that end effector 300 is ready to expel fasteners therefrom and must be depressed prior to actuating the control button 124 to commence firing. The user may rotate, articulate, and/or open end effector 300 at any point prior to firing the fasteners, each of the modes are described in further detail below.

End effector 300 and shaft assembly 200 are rotated clockwise by pressing the rocker switch 130 from right to left and counterclockwise by pressing the rocker switch 130 from left to right as viewed from the rear of surgical instrument 100. Rotation may occur prior to attachment of end effector 300. However, rotation is disabled while surgical instrument 100 is in firing mode and/or end effector 300 is clamped. The drive motor 166 is stopped when rotations per minute (RPM) reach 0 and remains stopped until the rocker switch 130 is released.

Articulation is enabled only after calibration of the shaft assembly 200 and while surgical instrument 100 is not in the firing mode. Articulation also can occur when end effector 300 is disconnected or end effector 300 is clamped, but at a slower rate. End effector 300 is articulated in left and right directions by pressing the rocker switch 128 in a left or right direction, respectively, as viewed from the rear of surgical instrument 100 and the cartridge assembly 308 of end effector 300 is facing upward.

End effector 300 may be centered, i.e., articulated to the center position when both control buttons 124 and 126 are pressed and surgical instrument 100 is not in firing mode. Once at the center position, articulation stops until the rocker switch 128 has been released and reactuated. The drive motor 166 is also stopped when a different button is pressed, a predetermined current limit is reached and/or end effector 300 has reached its articulation limit.

The anvil assembly 306 and the cartridge assembly 308 of end effector 300 are opened by pressing the control button 126. Opening continues until the control button 126 is released, a different button is pressed, a predetermined current limit is reached, and/or end effector 300 has reached its opening limit.

The anvil assembly 306 and the cartridge assembly 308 of end effector 300 are closed to contact tissue therebetween prior to engaging the firing mode. Prior to closing, surgical instrument 100 verifies whether the shaft assembly 200 coupled thereto has been calibrated as described above.

Closure is enabled only after calibration of the shaft assembly 200 and while surgical instrument 100 is not in the firing mode. Closure operation may occur when end effector 300 is disconnected, but at a slower rate. The anvil assembly 306 and the cartridge assembly 308 of end effector 300 are closed by pressing the control button 124. Closure continues until the control button 124 is released, a different button is pressed, a predetermined current limit is reached, and/or end effector 300 has reached its closure limit.

Once the anvil assembly 306 and the cartridge assembly 308 are closed, the firing sequence may be initiated. Prior to commencing firing, the safety switch 132 is engaged, which initiates a safety check algorithm. The safety algorithm verifies whether: 1) shaft assembly 200 is installed and calibrated; 2) usage counters of shaft assembly 200 and surgical instrument 100 are below their limits; 3) end effector 300 is installed; 4) end effector 300 has not been previously fired; 5) the charge level of the battery 156 is sufficient for firing; and 6) end effector 300 is in the clamped position. If all of the above conditions are satisfied, then surgical instrument 100 enters the firing mode and a corresponding status pattern is annunciated on the illumination member 116 as described above.

Firing is initiated by pressing the control button 124 when end effector 300 is clamped and the firing mode is engaged as described above. Continuously depressing the control button 124 advances the clamping member 365, which simultaneously ejects fasteners and cuts tissue. Firing continues until the control button 124 is released and/or end stop is detected. Firing progress, e.g., distance travelled by the clamping member 365, is indicated by the illumination member 116 as described below.

During firing, the main microcontroller 402 sets a normal speed current limit for the drive motor 166 by adjusting the limit control on a motor controller circuit coupled to the drive motor 166. While the drive motor 166 is set to the normal speed current limit, the main microcontroller 402 also monitors the rotational speed of the drive motor 166 and decreases the firing speed once a velocity threshold associated with the normal speed current limit is reached. The velocity threshold represents a floor value for the rotational speed range associated with the current limit. Once the speed is decreased to a lower speed, the main microcontroller 402 also sets a low speed current limit. As the drive motor 166 operates at the low speed current limit, the main microcontroller 402 also monitors the rotational speed of the drive motor 166 and stops the firing process once a velocity threshold associated with the low speed current limit is reached.

Pressing of the control button 126 at any time during the firing sequence, exists the firing mode and a corresponding indication is annunciated on the illumination member 116 as described above. Continually depressing the control button 126 while the control button 124 is released, retracts the clamping member 365 and once the clamping position is reached, end effector 300 is opened as described above.

After firing, a completion indication is annunciated on the illumination member 116 as described below. The firing counters stored within the ID chips 406 and 408 of surgical instrument 100 and shaft assembly 200, respectively, are incremented after firing as well. Autoclave counter for surgical instrument 100 is incremented upon shut off and for shaft assembly 200 after initial connection to surgical instrument 100 if it is not one of the last (e.g., five (5)) adapters detected since power up.

With reference to FIG. 32, the illumination member 116 disposed in the nose cone 114 (see FIGS. 1-3) is bisected by a horizontal plane "H" that defines an upper portion 116b above the horizontal plane "H" and a lower portion 116c below the horizontal plane "H" and by a vertical plane "V." The illumination member 116 includes white LEDs 117a, 117b, 117c, 117d, 117e disposed on the upper portion 116b of the illumination member 116. The LEDs 117a, 117b, 117c, 117d, 117e are utilized to indicate firing progress, e.g., distance travelled by the clamping member 365 as well as remaining service life of the of the surgical instrument 100, as described in further detail below.

The illumination member 116 also includes green LEDs 119a, 119b, 119c, 119d, 119e disposed on the lower portion 116c of the illumination member 116. The illumination member 116 also includes blue LEDs 121a and 121b disposed in the upper portion 116b of the illumination member 116 and at opposed sides thereof (i.e., at opposite sides of the vertical plane "V"). LEDs 119a-119e and 121a-121b are utilized to provide various status indicators. As described in detail below, the blue LEDs 121a and 121b are used to indicate error states. The nose cone 114 may include markings about the LEDs 119b, 119c, 119d associating them with the surgical instrument 100, shaft assembly 200, and the end effector 300, respectively. The illumination member 116 further includes red LEDs 123a, 123b, 123c also disposed on the upper portion 116b of the illumination member 116 interspersed between the white LEDs 117b, 117c, 117d.

The encoder microcontroller 412 signals the illumination member 116 to output a plurality of signal patterns indicative of specific operational statuses of surgical instrument 100, e.g., self-test failure, instrument 100 end of life indication, shaft assembly 200 uses remaining, calibration failure, state of readiness, progression of firing, instrument 100 uses remaining, etc. as shown in FIGS. 24A-24U.

Positioning of the LEDs about the circumference the nose cone 114 allows for the white LEDs 117a, 117b, 117c, 117d, 117e to be visible to a user having a line of sight that is above the horizontal plane "H." The green LEDs 119b, 119c, 119d disposed on the lower portion 116c of the illumination member 116 are visible to users other than the surgeon (e.g., surgical technologist) whose line of sight is below the horizontal plane "H." Since the blue LEDs 121a and 121b and green LEDs 119a and 119g are disposed on or above the horizontal plane "H," they are visible to the surgeon as well as other users. This allows the illumination member 116 to provide the surgeon with one set of status indicators, other users with another set of indicators, and the entire surgical team with a common set of indicators.

Figure 33A:
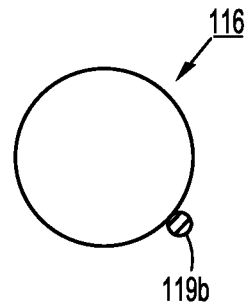
FIGS. 33A-T are front, schematic views of the illumination member of FIG. 32 illustrating various status patterns according to the present disclosure.

FIG. 33A shows a status pattern indicating that the power-on self-test is in progress and/or the control assembly 103 was activated during power-up after the battery 156 is inserted. The pattern is displayed by a flashing green LED 119b.

Figure 33B:
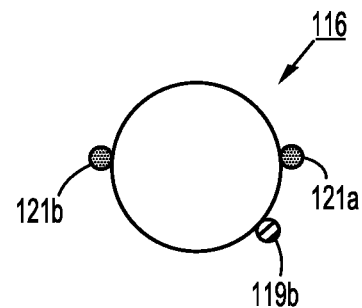

FIG. 33B shows a status pattern indicating that the self-test at power-on failed. The status pattern is displayed by solid blue LEDs 121a and 121b indicative of an error state and a flashing green LED 119b indicative that the error is pertaining to the surgical instrument 100. The pattern shown in FIG. 33B is indicative of failure of any of the components (e.g., communication interface 413, motors 164 and 166, storage memory 402b, usage counters, encoders 414 and 416, etc) tested during the power-on self-test described above.

Figure 33C:
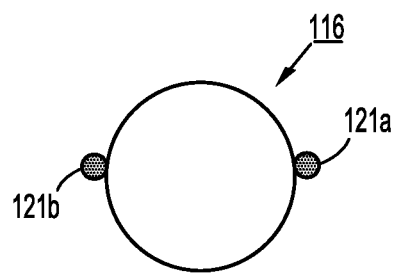

FIG. 33C shows a status pattern indicating that the battery 156 is defective. The status indicator is displayed by a solid blue LEDs 121a and 121b in response to the battery initialization testing as described above. The failure is indicative of any of the following problems with the battery 156 including, but not limited to, initialization failure, end of life, temperature outside acceptable ranges, low capacity, communication failure, and combinations thereof.

Figure 33D:
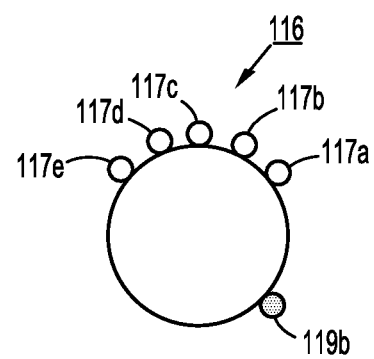
Figure 34A:
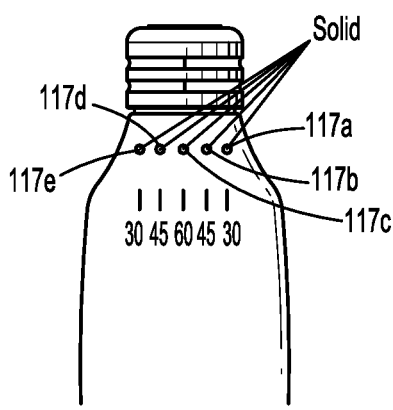
FIGS. 34A-D are top views of the surgical instrument 100 of FIG. 1 and the illumination member of FIG. 32 illustrating various status patterns according to the present disclosure.
Figure 34B:
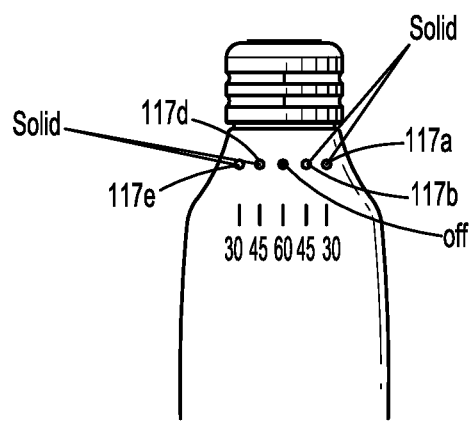
Figure 34C:
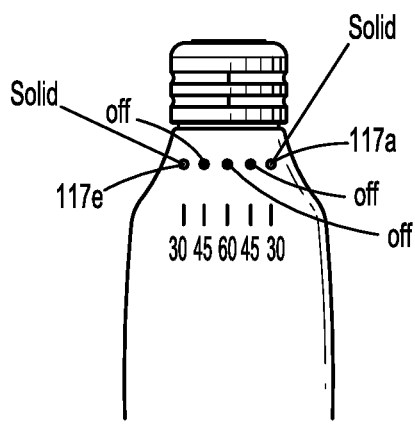

FIG. 33D shows a status pattern indicating that the self-test of the surgical instrument 100 was successful and provides the remaining usage of the surgical instrument 100. The status indicator is displayed by a solid LED 119b associated with the surgical instrument 100 and a varying number of solid LEDs 117a-117e, as shown in FIGS. 34A-34C. With reference to FIG. 34A, all of the LEDs 117a-117e are activated, which is indicative of a high number, or above an upper limit (e.g., more than 15) of uses still remaining. With reference to FIG. 34B, the LEDs 117a, 117b, 117d, 117e are activated, with the LED 117c being turned off, which is indicative of a medium number of uses remaining, namely between a lower limit and the upper limit (e.g., between 5 and 15). With reference to FIG. 34C, the LEDs 117a and 117e are activated and the LEDs 117b, 117c, 117d being turned off, which is indicative of a low number of uses remaining, namely, low value or below.

Figure 33E:
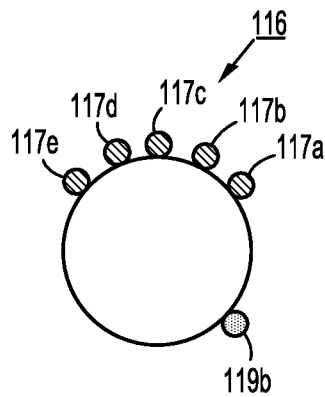

FIG. 33E shows a status pattern indicating a number of uses remaining of the surgical instrument 100 when the number of uses is below the lower limit. The status indicator may be triggered by pressing both control buttons 124 and 126 simultaneously after the remaining uses indicators described above with respect to FIGS. 33D and 34A-D are shown. Upon activating the control buttons 124 and 126, the LED 119b is illuminated solidly and the LEDs 117a-117e are flashed the number of times corresponding to the remaining number of uses.

Figure 33F:
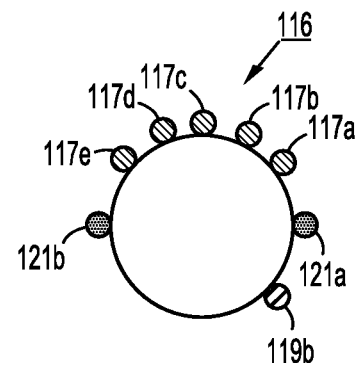
Figure 34D:
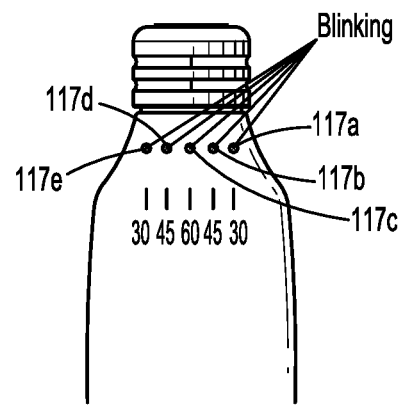

FIGS. 33F and 34D show a status pattern indicative of end of life of the surgical instrument 100. The status indicator is displayed by flashing all of the LEDs 117a-117e, a solid illumination of LEDs 121a and 121b, and a flashing LED 119b.

Figure 33G:
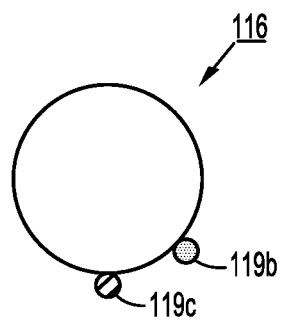

FIG. 33G shows a status pattern indicating that the shaft assembly 200 may be coupled to the surgical instrument 100. The status indicator is displayed by a solid illumination of LED 119b that is associated with the surgical instrument 100 and a flashing LED 119c that is associated with the shaft assembly 200.

Figure 33H:
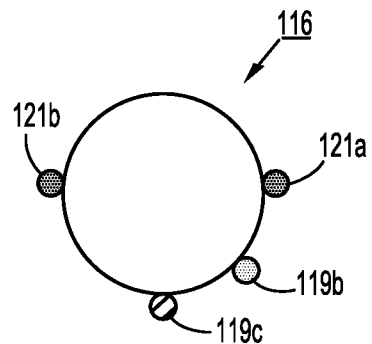

FIG. 33H shows a status pattern indicative of a calibration failure of the shaft assembly 200. The status indicator is displayed by a solid illumination of blue LEDs 121a and 121b indicative of an error state, a solid illumination of LED 119b that is associated with the surgical instrument 100 and a flashing LED 119c that is associated with the shaft assembly 200. The failure is indicative of any of the following problems with the shaft assembly 200 including, but not limited to, time-out during articulation end-stop detection, time-out during firing rod end-stop detection, usage counter of the shaft assembly 200 over limit, and combinations thereof.

Figure 33I:
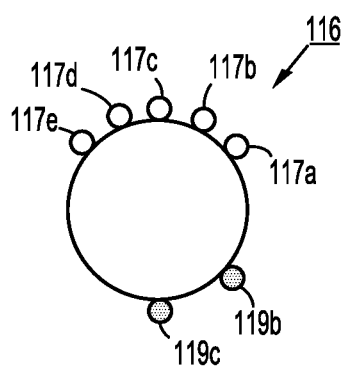

FIG. 33I shows a status pattern indicative that the calibration of the shaft assembly 200 was successful and provides the remaining usage of the shaft assembly 200. The status indicator is displayed by a solid illumination of LED 119b associated with the surgical instrument 100, a solid illumination of LED 119c associated with the shaft assembly 200, and a varying number of solid illumination of LEDs 117a-117e, as shown in FIGS. 34A-C. With reference to FIG. 34A, all of the LEDs 117a-117e are activated, which is indicative of a high number, or above an upper limit (e.g., more than 15) of uses still remaining. With reference to FIG. 34B, the LEDs 117a, 117b, 117d, 117e are activated, with the LED 117c being turned off, which is indicative of a medium number of uses remaining, namely between a lower limit and the upper limit (e.g., between 5 and 15). With reference to FIG. 34C, the LEDs 117a and 117e are activated and the LEDs 117b, 117c, 117d are turned off, which is indicative of a low number of uses remaining, namely, low value or below.

Figure 33J:
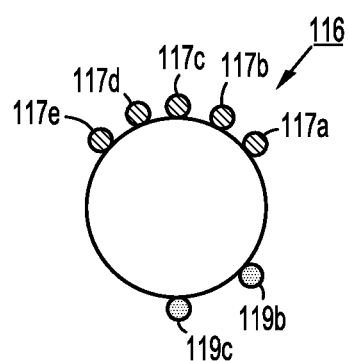

FIG. 33J shows a status pattern indicating a number of uses of the shaft assembly 200 remaining when the number of the remaining uses is below the lower limit. The status indicator may be triggered by pressing both control buttons 124 and 126 simultaneously after the remaining uses indicators described above with respect to FIGS. 33I and 34A-D are shown. Upon activating the control buttons 124 and 126, the LEDs 119b and 119c are illuminated solid and the LEDs 117a-117e are flashed the number of times corresponding to the remaining number of uses.

Figure 33K:
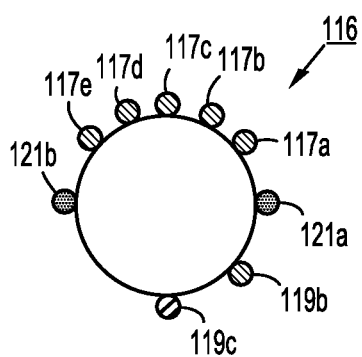

FIGS. 33K and 34D show a status pattern indicative of end of life of the shaft assembly 200. The status indicator is displayed by flashing all of the LEDs 117a-117e, solidly illuminating LEDs 121a and 121b, solidly illuminating LED 119b, and a flashing LED 119c.

Figure 33L:
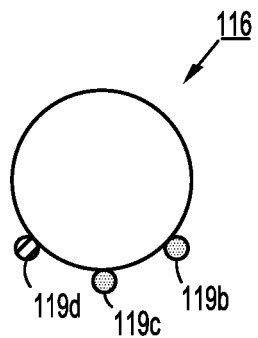

FIG. 33L shows a status pattern indicating that the end effector 300 may be coupled to the shaft assembly 200. The status indicator is displayed by a solid illumination of LED 119b that is associated with the surgical instrument 100, a solid illumination of LED 119c that is associated with the shaft assembly 200, and a flashing LED 119d that is associated with the end effector 300.

Figure 33M:
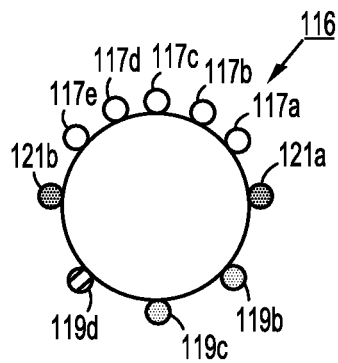

FIG. 33M shows a status pattern indicative of a failure of the end effector 300. The status indicator is displayed by a solid illumination of LEDs 119b, 119c, 121a, 121b, 117a-117c, and a flashing LED 119d. The failure is indicative of any of the following problems with the end effector 300 including, but not limited to, post-firing retraction beyond full clamp.

Figure 33N:
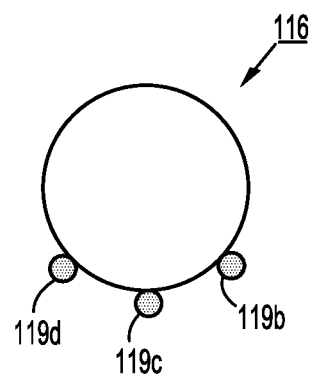

FIG. 33N shows a status pattern indicative that the clamp test of the end effector 300 was successful by a solid illumination of LEDs 119b, 119c, 119d.

Figure 33O:
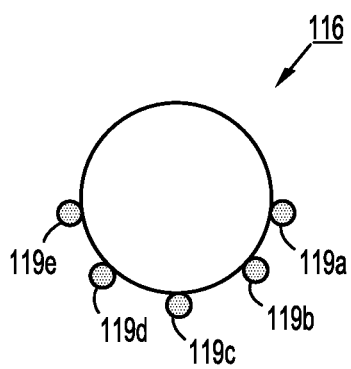

FIG. 33O shows a status pattern indicative of the end effector 300 being fully clamped (e.g., ready to engage the firing mode). The status indicator is displayed by a solid illumination of LEDs 119a-119e.

Figure 33P:
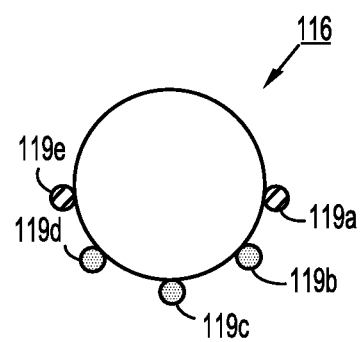

FIG. 33P shows a status pattern indicative of the system 10 being in firing mode. The status indicator is displayed by a solid illumination of LEDs 119b, 119c, 119d and flashing LEDs 119a and 119e.

FIGS. 33Q-T show status patterns indicative of the firing progress of the end effector 300. Similarly to the firing mode indication of FIG. 33P, LEDs 119b, 119c, 119d are solidly illuminated and LEDs 119a and 119e are flashing, while the LEDs 117a-117e are sequentially activated from the outside (e.g., LEDs 117a and 117e) until all are solidly illuminated, indicating completion of the firing progress. The nose cone 114 may be marked with distance markers (e.g., 30 mm for LEDs 119a and 119e, 45 mm for LEDs 119b and 119d, and 60 mm for LED 119c) as shown in FIGS. 34A-D.

Figure 33Q:
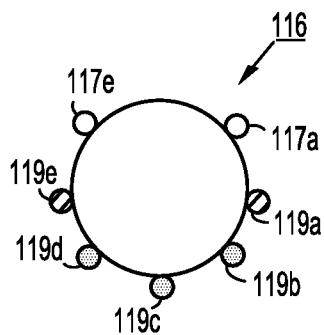
Figure 33R:
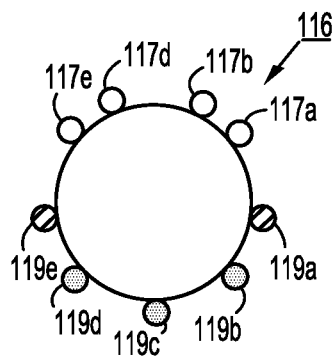
Figure 33S:
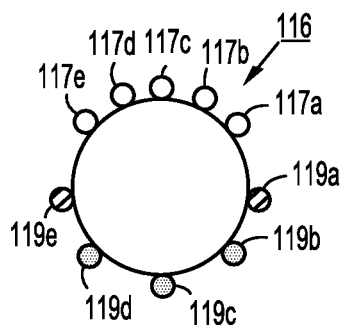

FIG. 33Q shows the outside LEDs 119a and 119e being activated at the beginning of the firing process as the clamping member 365 commences its travel (e.g., 30 mm). FIG. 33R shows the LEDs 119a, 119b, 119d, 119e being illuminated as the clamping member 365 is at (e.g., 45 mm). FIG. 33S shows all of the LEDs 119a-119e being illuminated as the clamping member 365 is fully extended (e.g., 60 mm).

Figure 33T:
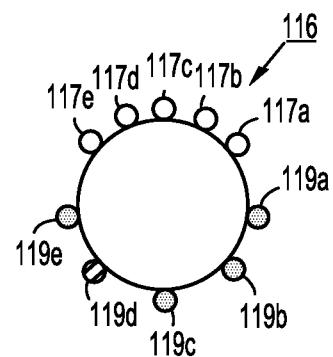

FIG. 33T shows a status pattern indicative of the retraction sequence of the clamping member 365 after the firing process is complete. The status indicator is displayed by a solid illumination of LEDs 117a-117e, solid LEDs 119a, 119b, 119c, 119e, and a flashing LED 119d associated with the end effector 300.

It will be understood that various modifications may be made to the embodiments disclosed herein. For example, the instrument 100 need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A surgical instrument, comprising:
    an end effector;
    an elongated body configured to couple to a proximal portion of the end effector, the elongated body including:
        an actuation bar movable upon engagement of the end effector with the elongated body to secure the end effector to the elongated body;
        a release button coupled to the actuation bar such that the release button is movable by the actuation bar upon engagement of the end effector with the elongated body; and
        a sensor actuatable by the release button being moved by the actuation bar, the sensor configured to transmit a signal indicative of the end effector being secured to the elongated body; and
    a handle assembly coupled to a proximal portion of the elongated body and configured to receive the signal.

2. The surgical instrument according to claim 1, wherein the end effector is a jaw assembly and defines a first longitudinal axis and including a first jaw and a second jaw moveable relative to the first jaw.

3. The surgical instrument according to claim 2, wherein the elongated body defines a second longitudinal axis, wherein the end effector is configured to articulate about an articulation axis transverse to the second longitudinal axis relative to the elongated body.

4. The surgical instrument according to claim 3, wherein the handle assembly includes at least one motor mechanically coupled to the end effector.

5. The surgical instrument according to claim 4, wherein the handle assembly includes a control assembly including a first control button and a second control button.

6. The surgical instrument according to claim 5, wherein actuation of the first control button moves the second jaw in approximation relative to the first jaw and actuating the second control button moves the second jaw away from the first jaw, and actuating the first and second control buttons moves the end effector to a centered position in which the first and second longitudinal axes are substantially aligned.

7. The surgical instrument according to claim 1, wherein the actuation bar includes a distal portion defining a window and a finger extending distally from distal portion.

8. The surgical instrument according to claim 7, wherein the actuation bar further includes a proximal portion having an opening configured to engage the release button.

9. The surgical instrument according to claim 7, wherein the finger includes a proximal cam surface, a distal large tab, and a distal small tab.

10. The surgical instrument according to claim 7, wherein the elongated body includes a lock mechanism having a lockout and a biasing member configured to push the actuation bar distally.

11. The surgical instrument according to claim 10, wherein the end effector includes at least one lug and the elongated body includes a bayonet connection mount configured to receive the at least one lug.

12. The surgical instrument according to claim 11, wherein the end effector is coupled to the elongated body by rotating the end effector.

13. The surgical instrument according to claim 12, wherein rotation of the end effector initially pushes the actuation bar proximally and upon completion of the rotation the actuation bar is moved distally by the biasing member and the finger retains the at least one lug within the elongated body.

* * * * *